(12) United States Patent
Kambe et al.

(10) Patent No.: US 12,112,484 B2
(45) Date of Patent: Oct. 8, 2024

(54) METHOD FOR GENERATING LEARNING MODEL AND PROGRAM

(71) Applicant: HOYA CORPORATION, Tokyo (JP)

(72) Inventors: Chihiro Kambe, Tokyo (JP); Kohei Iketani, Saitama (JP)

(73) Assignee: HOYA CORPORATION, Tokyo (JP)

( * ) Notice: Subject to any disclaimer, the term of this patent is extended or adjusted under 35 U.S.C. 154(b) by 402 days.

(21) Appl. No.: 17/627,327

(22) PCT Filed: Nov. 18, 2020

(86) PCT No.: PCT/JP2020/042991
§ 371 (c)(1),
(2) Date: Jan. 14, 2022

(87) PCT Pub. No.: WO2021/111879
PCT Pub. Date: Jun. 10, 2021

(65) Prior Publication Data
US 2022/0277461 A1  Sep. 1, 2022

(30) Foreign Application Priority Data

Dec. 5, 2019 (JP) ................................ 2019-220681

(51) Int. Cl.
*G06T 7/20* (2017.01)
*G06N 20/00* (2019.01)
(Continued)

(52) U.S. Cl.
CPC .............. *G06T 7/20* (2013.01); *G06N 20/00* (2019.01); *G06T 7/0012* (2013.01); *G16H 30/40* (2018.01);
(Continued)

(58) Field of Classification Search
None
See application file for complete search history.

(56) References Cited

U.S. PATENT DOCUMENTS

| 6,454,776 B1 | 9/2002 | Tajima et al. |
| 2016/0073927 A1* | 3/2016 | Akimoto ............ A61B 1/00194 600/109 |
| 2018/0065248 A1* | 3/2018 | Barral ..................... G06N 20/00 |
| 2018/0108138 A1* | 4/2018 | Kluckner ................. G06T 7/11 |

(Continued)

FOREIGN PATENT DOCUMENTS

| JP | 10-027089 | 1/1998 |
| JP | 2001-000448 | 1/2001 |

(Continued)

OTHER PUBLICATIONS

Dec. 20, 2022 Japanese Office Action in JP 2021-562557 and English translation thereof.

(Continued)

*Primary Examiner* — Tsung Yin Tsai
(74) *Attorney, Agent, or Firm* — GREENBLUM & BERNSTEIN, P.L.C.

(57) ABSTRACT

There is provided a method for generating a learning model, the method including: acquiring an endoscopic image captured by an endoscope and manipulation information regarding a manipulation of an endoscope operator in each stage of operation of the endoscope by the endoscope operator operating the endoscope; and generating a learning model learned so as to output the manipulation information of a next stage in a case where the endoscopic image and the manipulation information are input, based on training data including the acquired endoscopic image and manipulation information, and the manipulation information of the next stage.

19 Claims, 21 Drawing Sheets

(51) Int. Cl.
*G06T 7/00* (2017.01)
*G16H 30/40* (2018.01)

(52) U.S. Cl.
CPC .............. *G06T 2207/10028* (2013.01); *G06T 2207/10068* (2013.01); *G06T 2207/20081* (2013.01); *G06T 2207/20084* (2013.01); *G06T 2207/30196* (2013.01)

(56) References Cited

U.S. PATENT DOCUMENTS

| | | | |
|---|---|---|---|
| 2019/0125361 A1* | 5/2019 | Shelton, IV | A61B 17/1227 |
| 2020/0090548 A1 | 3/2020 | Kimura et al. | |
| 2020/0129043 A1 | 4/2020 | Takayama et al. | |
| 2020/0138527 A1 | 5/2020 | Sekiguchi et al. | |
| 2020/0305682 A1* | 10/2020 | Kyperountas | G16H 20/40 |
| 2020/0312464 A1 | 10/2020 | Shiraga | |
| 2022/0257102 A1* | 8/2022 | Weeks | G06T 7/12 |

FOREIGN PATENT DOCUMENTS

| | | |
|---|---|---|
| JP | 2010-108388 | 5/2010 |
| JP | 2015-519596 | 7/2015 |
| JP | 2017-102755 | 6/2017 |
| JP | 2018-142815 | 9/2018 |
| JP | 2018-169720 | 11/2018 |
| WO | 2018/211674 | 11/2018 |
| WO | 2018/216283 | 11/2018 |
| WO | 2019/008726 | 1/2019 |
| WO | 2019/111512 | 6/2019 |

OTHER PUBLICATIONS

International Search Report issued in International Bureau of WIPO Patent Application No. PCT/JP2020/042991, dated Feb. 2, 2021, along with an English translation thereof.

* cited by examiner

FIG. 3

| HISTORY ID | DATE AND TIME | ENDOSCOPIC IMAGE | DETECTION VALUE | OPERATION DATA | | |
|---|---|---|---|---|---|---|
| | | | | INSERTION AMOUNT | BENDING DIRECTION | LIGHT AMOUNT |
| 1 | 8:10:00 | A01.mp4 | *** | *** | *** | *** |
| 2 | 8:10:10 | A01.mp4 | *** | *** | *** | *** |
| 2 | 8:10:20 | A01.mp4 | *** | *** | *** | *** |
| ... | | | | | | |

521

METHOD FOR GENERATING LEARNING MODEL AND PROGRAM

TECHNICAL FIELD

The present disclosure relates to a method for generating a learning model, a program, a manipulation support system, an information processing device, an information processing method, and a processor for an endoscope.

BACKGROUND ART

In a medical facility, support according to an ability of a person in charge is performed such that a difference in manipulation contents due to a difference in an experience and a skill of the person in charge does not occur. In order to perform the support according to the ability of the person in charge, it is important to appropriately grasp the manipulation contents, a manipulation ability, and the like of the person in charge and present support contents based on these pieces of information. As a method for determining the manipulation ability, Patent Literature 1 discloses a method for analyzing sensor data of a motion of a user, which is received from a motion sensing camera, to acquire ability data of the user while the manipulation is performed, and determine an ability measurement by comparing the acquired ability data with an ability model.

CITATION LIST

Patent Literature

Patent Literature 1: JP 2015-519596 A

SUMMARY OF INVENTION

Technical Problem

However, the method disclosed in Patent Literature 1 has a problem that sufficient data cannot be acquired in the manipulation of the endoscope, and there is a concern that appropriate support information for supporting the manipulation of the endoscope is not presented.

An object of the present disclosure is to provide a method for generating a learning model that outputs appropriate information for supporting a manipulation based on manipulation information in the manipulation of the endoscope, a program, a manipulation support system, an information processing device, an information processing method, and a processor for an endoscope.

Solution to Problem

According to an aspect of the present disclosure, there is provided a method for generating a learning model, the method including: acquiring an endoscopic image captured by an endoscope and manipulation information regarding a manipulation of an endoscope operator in each stage of operation of the endoscope by the endoscope operator operating the endoscope; and generating a learning model learned so as to output the manipulation information of a next stage in a case where the endoscopic image and the manipulation information are input, based on training data including the acquired endoscopic image and manipulation information, and the manipulation information of the next stage.

Advantageous Effects of Invention

According to the present disclosure, it is possible to output appropriate information for supporting the manipulation based on the manipulation information in the manipulation of the endoscope.

BRIEF DESCRIPTION OF DRAWINGS

FIG. 3 is a diagram illustrating a contents example of information stored in a history DB.

DESCRIPTION OF EMBODIMENTS

The present invention will be specifically described with reference to the drawings illustrating embodiments of the invention.

First Embodiment

Figure 1:
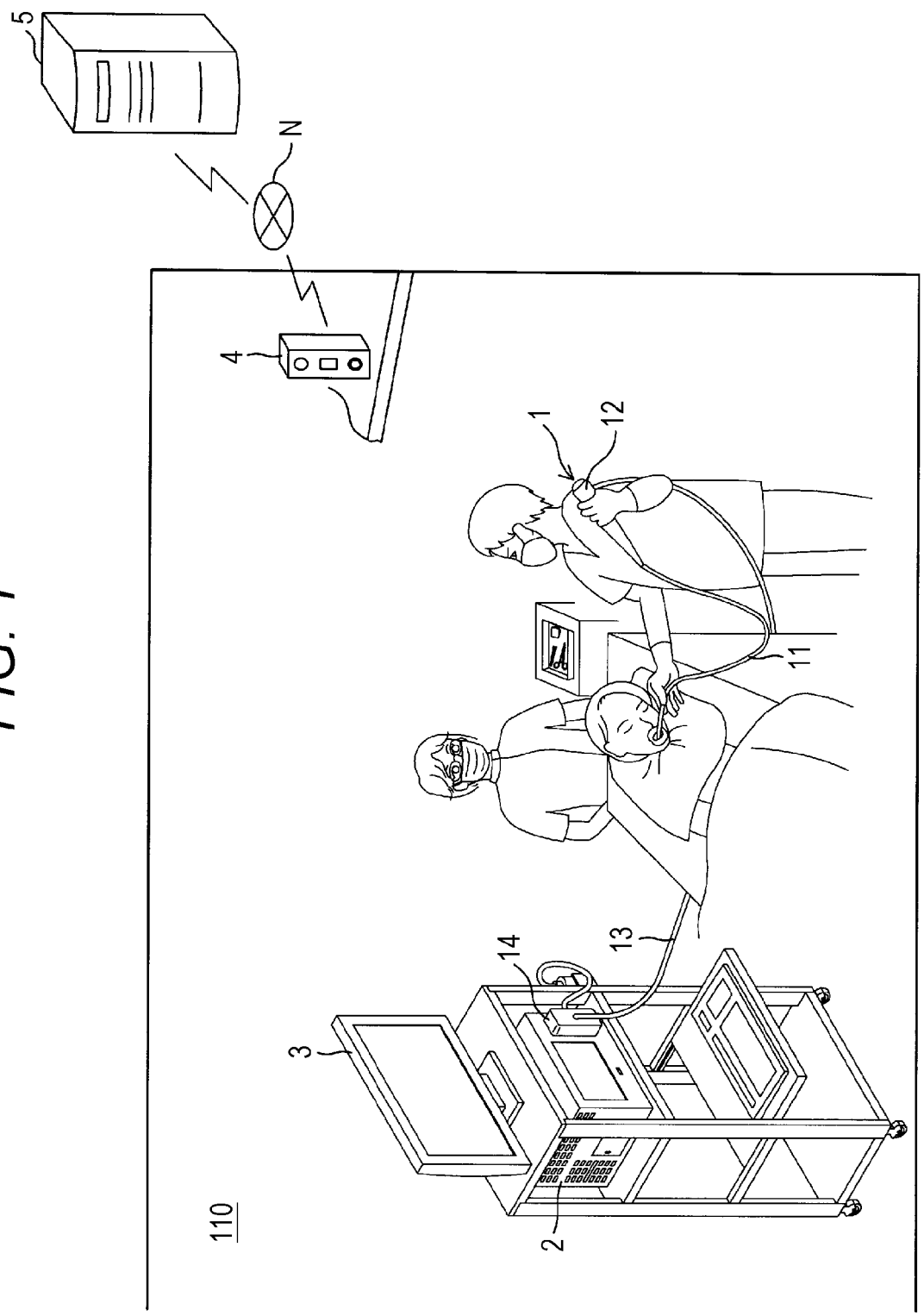
FIG. 1 is a schematic view of a learning model generation system according to a first embodiment.

FIG. 1 is a schematic view of a learning model generation system 110 according to a first embodiment. The learning model generation system 110 includes an endoscope 1, a processor 2 for an endoscope, a detection device 4, and an information processing device 5. A display device 3 is connected to the processor 2 for an endoscope. The endoscope 1, the processor 2 for an endoscope, and the display device 3 are connected to each other via a connector, and transmit and receive an electric signal, a video signal, and the like. The processor 2 for an endoscope and the detection device 4 are communicatively connected to the information processing device 5 via a network N such as a local area network (LAN).

The endoscope 1 is, for example, an endoscope for an upper digestive tract or a large intestine endoscope. The endoscope 1 includes an insertion tube 11 and a connector unit 14 connected to the insertion tube 11 via an operation unit 12 and a universal cord 13, and is used in a state of being connected to the processor 2 for an endoscope by the connector unit 14.

The insertion tube 11 is long and is a portion to be inserted into a hollow organ such as a digestive tract of a subject. At a distal end of the insertion tube 11, an image sensor that receives light reflected from an object through an observation window and performs photoelectric conversion is disposed. The image sensor includes a charge coupled device (CCD) image sensor, a charge modulation device (CMD) image sensor, a complementary metal oxide semiconductor (CMOS) image sensor, or the like. An electric signal generated by the photoelectric conversion is subjected to signal processing such as A/D conversion and noise removal by a signal processing circuit (not illustrated), and is output to the processor 2 for an endoscope. A channel outlet connected to a channel inlet to be described later, a nozzle that ejects and sucks cleaning water and air, and the like are provided at the distal end of the insertion tube 11. Physical quantity detection devices such as a three-axis acceleration sensor, a gyro sensor, a geomagnetic sensor, and a magnetic coil sensor may be mounted on the insertion tube 11, and when the endoscope 1 is inserted into a body of the subject, detection results from these physical quantity detection devices may be acquired.

The operation unit 12 is provided to be held by an endoscope operator to perform various manipulations, and includes a release button, an angle knob for bending the distal end of the endoscope, and the like. The operation unit 12 receives an input of an operation instruction signal of a peripheral device, such as air supply, water supply, or gas supply. The operation unit 12 further includes a channel inlet. A forceps plug having an insertion port for inserting a treatment tool or the like is fixed to the channel inlet. The treatment tool inserted from the insertion port is, for example, forceps, a gripping tool, an injection needle, a biopsy needle, a snare, a clamp, scissors, a scalpel, an incision instrument, an endoscopic stapler, a tissue loop, a clip applier, a suture delivery instrument, or the like.

The universal cord 13 is long, and has a first end connected to the operation unit 12 and a second end connected to the connector unit 14. A fiber bundle, a cable bundle, an air supply tube, a water supply tube, and the like, which extend from the insertion tube 11 and the operation unit 12, are inserted into the universal cord 13. One end of the fiber bundle or the like is disposed in a communication connector (not illustrated) of the connector unit 14 and connected to the processor 2 for an endoscope.

The processor 2 for an endoscope is an information processing device that performs various image processing such as gamma correction, white balance correction, and shading correction on an image captured by the image sensor of the endoscope 1 to generate an endoscopic image that can be easily seen by a user, and outputs the endoscopic image to the display device 3.

The display device 3 is a liquid crystal display, or an organic electroluminescence (EL) display. The display device 3 displays an image or the like output from the processor 2 for an endoscope.

The detection device 4 is a detection device that detects 3D data of a motion of the endoscope operator of the endoscope 1, and is, for example, a 3D laser sensor. The detection device 4 is connected to the information processing device 5 in a wired or wireless manner. The detection device 4 transmits the detected detection value to the information processing device 5. The 3D laser sensor detects a distance and a direction to an object at a predetermined resolution by, for example, a time of flight (TOF) method, and outputs the 3D data indicating a three-dimensional position coordinate of each point on the object. The 3D laser sensor is configured such that an angle of view indicating a detection range in a horizontal direction and a vertical direction and a direction of a center line connecting a center of the detection range and the 3D laser sensor can be changed. The detection device 4 can maintain a high resolution even in a case where a position of a detection object changes, for example, by adjusting the angle of view and the direction based on the position of the detection object. For example, the detection device 4 is set such that a movement range of both hands and both arms for operating the endoscope 1 of the endoscope operator is set as an angle of view. The detection device 4 may be set such that a range including the entire body of the endoscope operator is set as an angle of view.

The detection value transmitted from the detection device 4 to the information processing device 5 is a 3D data group in which a 3D coordinate value of each point included in a point group on the object detected by the detection device 4 at each time is represented in a sensor coordinate system. The information processing device 5 calculates a coordinate value for each part of the endoscope operator from the acquired 3D data group. As a method for calculating the coordinate value of each part of a human body from the 3D data group, for example, a method described in JP 2018-169720 A may be used.

Each part of the endoscope operator is a part of the human body such as a joint serving as a feature point for specifying a posture of the detection object. For example, each part is a right hand, a right wrist, a right elbow, a right shoulder, a left hand, a left wrist, a left elbow, a left shoulder, or the like. Each part may include a head, a center of a shoulder, a spine, a right knee, a right ankle, a right foot, a left knee, a left ankle, a left foot, and the like. As the coordinate value of each part, for example, a vector indicating an axial direction of each part and a quaternion indicating rotation can be used. By detecting the three-dimensional position coordinate in each part of the endoscope operator by using the detection device 4, detailed motions for the endoscope operation, such as a motion of a finger and twisting of a wrist of the endoscope operator are detected with high accuracy.

Note that the detection device 4 is not limited to the 3D laser sensor. The detection device 4 only needs to detect the motion of the endoscope operator, and may be, for example, an image sensor or the like. The detection device 4 may be a stereo camera including a plurality of the image sensors.

The information processing device 5 is, for example, a server computer. The information processing device 5 acquires information regarding the manipulation of the endoscope from the processor 2 for an endoscope and the detection device 4, and generates a learning model that outputs manipulation information for supporting the manipulation of the endoscope operator based on the acquired information. In the first embodiment, the information processing device 5 will be described as one server computer, but functions or processing may be distributed among a plurality of the server computers, or the information processing device 5 may be one of a plurality of the server computers (instances) virtually generated in one large computer.

Figure 2:
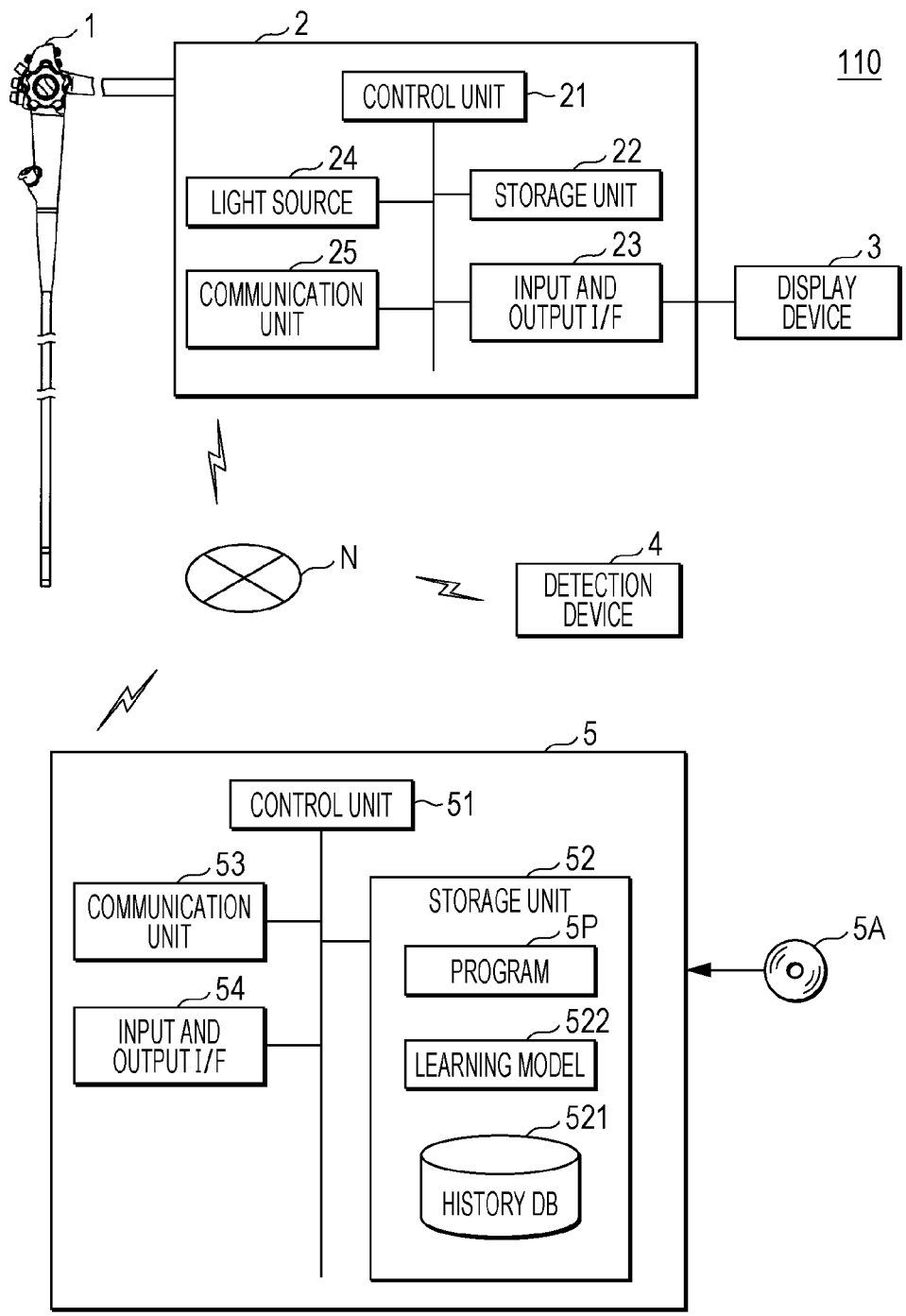
FIG. 2 is a block diagram illustrating a configuration example of a learning model generation system.

FIG. 2 is a block diagram illustrating a configuration example of the learning model generation system 110. The processor 2 for an endoscope includes a control unit 21, a storage unit 22, an input and output interface (I/F) 23, a light source 24, and a communication unit 25. Each configuration is connected by a bus. In the present embodiment, the processor 2 for an endoscope will be described as one information processing device, but processing may be performed by distributing the processor 2 for an endoscope into a plurality of processors, or the processor may be configured by a virtual machine.

The control unit 21 includes an arithmetic processing device such as a central processing unit (CPU), a microprocessing unit (MPU), or a graphics processing unit (GPU). The control unit 21 executes processing by using a memory such as a built-in read only memory (ROM) or a built-in random access memory (RAM). The control unit 21 performs various information processing, control processing, and the like related to the processor 2 for an endoscope by reading and executing the program stored in the storage unit 22. The control unit 21 is described as a single processor in FIG. 2, but the control unit 21 may be a multiprocessor.

The storage unit 22 includes, for example, a non-volatile memory such as a hard disk or a solid state drive (SSD). The storage unit 22 stores the program and data referred to by the control unit 21.

The input and output I/F 23 is a communication interface for serial communication with an external device connected to the processor 2 for an endoscope. For example, the display device 3 such as a display and an input device such as a keyboard are connected to the input and output I/F 23. The control unit 21 outputs, to the display device 3, a result of information processing performed based on an input signal generated in response to an external operation to the input device.

The light source 24 includes a light source that emits illumination light used for illuminating an observation target. The light source 24 is, for example, a semiconductor light source such as a multi-color light emitting diode (LED) having a different wavelength range, a combination of a laser diode and a phosphor, or a xenon lamp. Turning on and off of the light source 24 and change of luminance are controlled by the control unit 21. Note that in the present embodiment, the processor 2 for an endoscope is an integrated type of light source, but the present invention is not limited to this. For example, the processor 2 for an endoscope may be of a light source separation type in which a light source device is separated from the processor 2 for an endoscope.

The communication unit 25 is a communication interface that implements communication via the network N. The control unit 21 can be communicatively connected to the information processing device 5 via the network N by the communication unit 25. Note that the communication interface included in the communication unit 25 may perform communication by using, for example, a wireless communication module including an antenna for short-range wireless communication such as Bluetooth (registered trademark) or WiFi (registered trademark). Furthermore, the communication unit 25 may include a wired communication interface such as a USB.

The information processing device 5 includes a control unit 51, a storage unit 52, a communication unit 53, and an input and output I/F 54. The control unit 51 includes one or a plurality of arithmetic processing devices such as a CPU, an MPU, and a GPU. The control unit 51 executes processing by using a memory such as a built-in ROM and RAM. The control unit 51 performs various information processing, control processing, and the like related to the information processing device 5 by reading and executing a program 5P stored in the storage unit 52.

The storage unit 52 includes, for example, a non-volatile memory such as a hard disk or an SSD. The storage unit 52 stores the program 5P and also stores other programs and data to be referred to by the control unit 51. The program 5P stored in the storage unit 52 may be a program read from a recording medium 5A capable of being read by the information processing device 5. Furthermore, the program 5P may be a program downloaded from an external computer (not illustrated) connected to a communication network (not illustrated) and be stored in the storage unit 52. The storage unit 52 stores a history database (DB) 521 and a learning model 522. The learning model 522 is an identifier that identifies manipulation information that supports the manipulation of the endoscope of the endoscope operator, and is a learning model generated by machine learning. Note that the storage unit 52 may be configured by a plurality of storage devices, or may be an external storage device connected to the information processing device 5.

The communication unit 53 is a communication interface that implements communication via the network N. The control unit 51 can be communicatively connected to the processor 2 for an endoscope and the detection device 4 via the network N by the communication unit 53.

The input and output I/F 54 is compliant with, for example, a communication standard such as USB or D-SUB, and is a communication interface for performing serial communication with an external device connected to the input and output I/F 54. For example, an output device such as a display and an input device such as a keyboard are connected to an input and output I/F 64.

FIG. 3 is a diagram illustrating a contents example of information stored in the history DB 521. The information processing device 5 collects manipulation information regarding the manipulation of the endoscope operator skilled in operating the endoscope 1, and stores the manipulation information in the history DB 521. The history DB 521 stores, for example, the manipulation information including Date and Time, Endoscopic Image, Detection Value, and Operation Data in association with a history ID for identifying the history information.

In the Date and Time, a date and time when an endoscope manipulation is performed is recorded. In FIG. 3, as an example, data is recorded in units of 10 milliseconds. In the Endoscopic Image, an endoscopic image captured by the endoscope 1 is recorded. The endoscopic image is a still image or a moving image configured of a plurality of frames of the still images. The Detection Value is state data indicating motions of both hands, both arms, and the like of the endoscope operator. In the Detection Value, for example, a coordinate value of each part of the endoscope operator, which is calculated from the 3D data group or the 3D data group, at the time of each date and time detected by the detection device 4 and each part are recorded in association with each other. The Operation Data is information regarding operation data of the distal end of the endoscope 1, and may include information regarding an insertion amount of the endoscope 1 into the body, a bending direction of the distal end of the endoscope 1, a light amount of the light source 24, and the like. As the insertion amount of the endoscope 1 into the body, a detection value detected from the physical quantity detection device such as the three-axis acceleration sensor provided in the insertion tube 11 of the endoscope 1 is recorded. As the bending direction of the endoscope 1, operation data of a bending button of the operation unit 12, which is obtained from the processor 2 for an endoscope, is recorded. As the light amount of the light source 24, luminance control data for the light source 24, which is obtained from the processor 2 for an endoscope, is recorded. Note that FIG. 3 is an example, and the contents stored in the history DB 521 are not limited.

Figure 4:
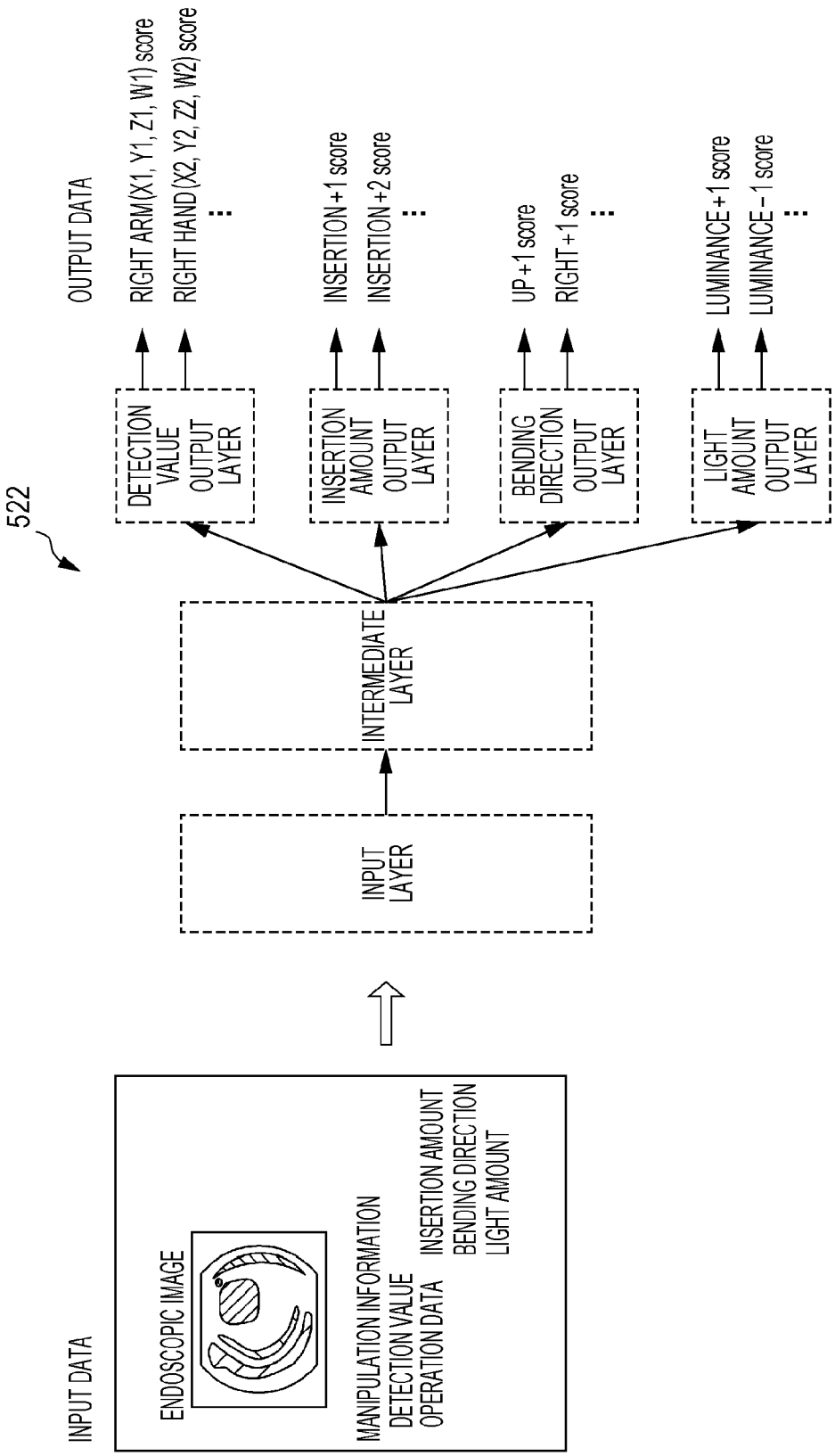
FIG. 4 is an explanatory diagram for explaining a configuration of a learning model.

FIG. 4 is an explanatory diagram for explaining a configuration of the learning model 522. The learning model 522 is generated and learned by deep learning using a neural network. The learning model 522 is, for example, a convolution neural network (CNN). In the example illustrated in FIG. 4, the learning model 522 includes an input layer that inputs endoscopic image data and manipulation information, an output layer that outputs manipulation information of a next stage for the manipulation being performed, and an intermediate layer that extracts feature amounts of the endoscopic image data and manipulation information. The intermediate layer includes a plurality of nodes that extract the feature amounts of the endoscopic image data and manipulation information, and passes image feature amounts extracted by using various parameters to the output layer. The intermediate layer may include a convolution layer, a pooling layer, a fully-connected layer, and the like. The learning model 522 has a plurality of the output layers that output the set manipulation information.

Input data input to the input layer of the learning model 522 are an endoscopic image captured by the endoscope 1 and manipulation information in a predetermined stage. The endoscopic image is a still image or a moving image configured of a plurality of frames of the still images. The manipulation information may include a detection value and operation data. The detection value is state data of both hands, both arms, and the like of the endoscope operator, which includes the 3D data group detected by the detection device 4 or a coordinate value for each part of the endoscope operator, which is calculated from the 3D data group. The operation data includes operation data such as an insertion amount, bending direction, and light amount of the endoscope 1. Note that in this case, the endoscopic image data may be input to the input layer via the convolution layer and a convolution layer (not illustrated).

Output data output from the output layer of the learning model 522 is manipulation information of the next stage for the manipulation being performed in a predetermined stage. For example, in a case where the input data is the endoscopic image and the manipulation information at the time tn, the output data is the manipulation information at the time tn+1. The learning model 522 includes a plurality of output layers that output, for example, a detection value, an insertion amount, a bending direction, and a light amount as the manipulation information. The output layer that outputs the detection value includes channels each corresponding to the set detection value, and outputs accuracy for each detection value as a score. The information processing device 5 can set the detection value having the highest score or the detection value having a score equal to or greater than a threshold as output data of the output layer that outputs the detection value. Note that the output layer may have one output node that outputs the most accurate detection value instead of having a plurality of output channels that output the accuracy of each detection value. Similarly, the output data of the insertion amount, the bending direction, and the light amount are output from the output layers of the insertion amount, the bending direction, and the light amount, respectively. As described above, in a case where the endoscopic image and the manipulation information in a predetermined stage are input, the learning model 522 outputs the manipulation information of the next stage.

The configuration in which the learning model 522 includes a plurality of the output layers has been described above, but the learning model 522 may include one output layer. The information processing device 5 may include a plurality of the learning models 522 each having the output layer that outputs the detection value, the insertion amount, the bending direction, and the light amount. In this case, the input data corresponding to the manipulation information to be output may be input to each learning model 522. For example, the input data input to the learning model 522 that outputs the detection value as the manipulation information may be only the endoscopic image and the detection value, or all of the endoscopic image, the detection value, and the operation data may be input.

In the above description, an example has been described in which the detection value that is the state data of both hands and both arms of the endoscope operator and the operation data that is the insertion amount, the bending direction, and the light amount are included as the manipulation information. However, the manipulation information input to and output from the learning model 522 is not limited. The manipulation by the operation of the endoscope 1 includes, for example, examination and observation of the digestive tract and the like of the subject by the endoscope 1, a manipulation by the treatment tool, and the like. The manipulation information may include these manipulation contents data.

For example, in a manipulation including resection of a lesion, the learning model 522 using the manipulation contents data as an input element may be configured to output the manipulation contents data such as injection of physiological saline as the manipulation information of the next stage in a case where the manipulation information to be input includes manipulation contents data indicating insertion of an injection needle as a treatment tool. Furthermore, the manipulation information may include operation data of air and water supply to the endoscope 1, parameters when image processing is performed on the endoscopic image used by the processor 2 for an endoscope, and the like. Furthermore, the manipulation information may include lesion data such as presence or absence and a state of the lesion corresponding to the endoscopic image. For example, the manipulation information output from the learning model 522 may include lesion data determined from the endoscopic image that is input data. Furthermore, the learning model 522 may include lesion data in the input manipulation information and output the manipulation information such as manipulation contents and light amount information which are associated with the lesion data.

Figure 5:
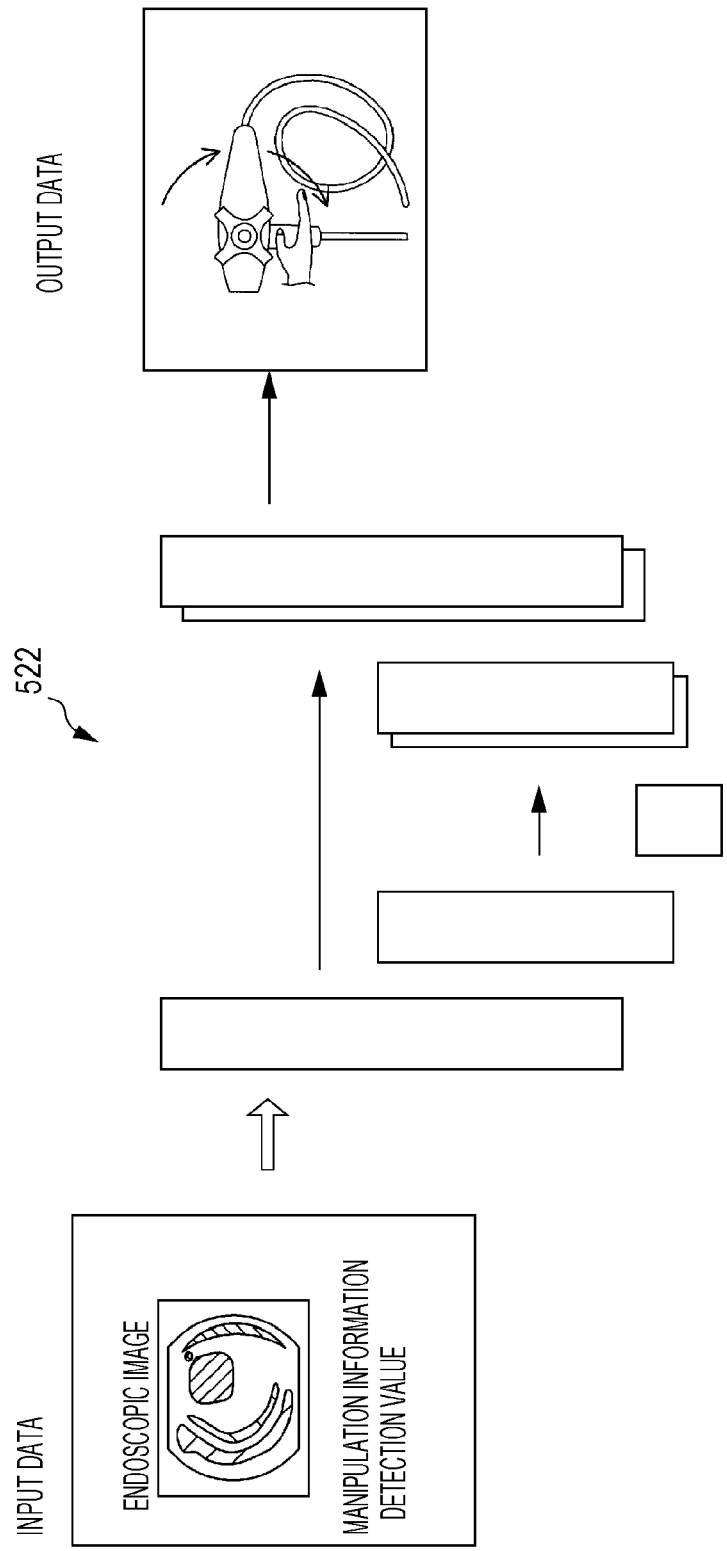
FIG. 5 is an explanatory diagram for explaining a different configuration of a learning model.

The learning model 522 may generate an image of the manipulation information of the next stage by using an algorithm such as U-Net. FIG. 5 is an explanatory diagram for explaining a different configuration of the learning model 522. The learning model 522 includes an encoder unit and a decoder unit. The encoder unit encodes the input data to extract a feature amount, and the decoder unit decodes the extracted feature amount to generate an image. The input data input to the input layer of the learning model 522 are the endoscopic image captured by the endoscope 1 and a detection value that is state data of both hands and both arms of the endoscope operator in a predetermined stage. The output data output from the output layer of the learning model 522 is an image indicating the states of both hands and both arms of the next stage which are generated based on the state data of both hands and both arms of the next stage of the predetermined stage. The image may be a 3D image based on the three-dimensional position coordinates.

The learning model 522 is not limited to the above example, and in a case where time series data is acquired, for example, a recurrent neural network (RNN) may be used. The learning model 522 may predict a plurality of pieces of the manipulation information of the next stage by using the RNN of Seq2Seq. Furthermore, the learning model 522 may be a model learned by a neural network other than the CNN or another algorithm.

Figure 6:
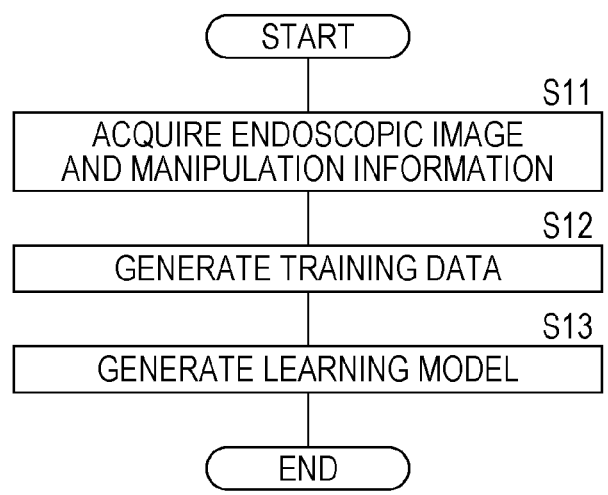
FIG. 6 is a flowchart illustrating an example of a processing procedure performed by an information processing device.

In the learning model generation system 110 configured as described above, machine learning processing of generating a learning model is executed. FIG. 6 is a flowchart illustrating an example of a processing procedure performed by the information processing device 5.

The control unit 51 of the information processing device 5 acquires the endoscopic image and the manipulation information in each operation stage of the endoscope 1 of the endoscope operator (step S11). The manipulation information includes the state data of both hands and both arms of the endoscope operator in each operation stage, and the operation data of the insertion amount, bending direction, and light amount of the endoscope 1. Specifically, the control unit 51 acquires the operation data such as the endoscopic image, the insertion amount, bending direction, and light amount of the endoscope 1 from the processor 2 for an endoscope. Furthermore, the control unit 51 acquires the detection value from the detection device 4.

The control unit 51 generates training data in which the acquired endoscopic image and the acquired manipulation information in each operation stage (for example, the stage at the time tn) are labeled with the manipulation information in the next stage (for example, the stage at the time tn+1) of each operation stage, which is recorded in the history DB 521 (step S12). In the history DB 521, a large amount of information in each operation stage of endoscopic examination performed by a skilled endoscope operator in the past is recorded. By using the large amount of data, the control unit 51 generates training data in which the manipulation information in the next stage is associated with each of the acquired endoscopic image and the acquired manipulation information in each operation stage.

By using the generated training data, the control unit 51 generates the learning model 522 that outputs the manipulation information in the next stage in a case where the endoscopic image and the manipulation information are input (step S13). Specifically, the control unit 51 inputs the endoscopic image and the manipulation information in a predetermined stage to the input layer of the neural network. The control unit 21 acquires a prediction value of the manipulation information in the next stage from the output layer. The control unit 51 optimizes a model parameter used for arithmetic processing in the intermediate layer such that the prediction value output from the output layer approaches a correct answer value by comparing the prediction value of the manipulation information with the manipulation information that is the correct answer value. By applying the optimized model parameter to the defined neural network, the learning model 522 can output the manipulation information in the next stage in a case where the endoscopic image data and the manipulation information are input. The control unit 51 stores the generated learning model 522 in the storage unit 52, and ends a series of processing.

The example in which the control unit 51 of the information processing device 5 executes a series of processing has been described above, but the present embodiment is not limited to this. A part or all of the processing described above may be executed by the control unit 21 of the processor 2 for an endoscope. That is, the processor 2 for an endoscope may substantially include the information processing device 5. Furthermore, the learning model 522 may be generated by the information processing device 5 and learned by the processor 2 for an endoscope. The control unit 51 of the information processing device 5 and the control unit 21 of the processor 2 for an endoscope may perform, for example, a series of processing in cooperation by performing communication between processes.

According to the present embodiment, the learning model 522, which outputs the manipulation information of the next stage in accordance with the endoscopic image and the manipulation information of an operation stage in the manipulation of the endoscope, is generated by using the training data including the operation data of the endoscope operator skilled in an operation manipulation of the endoscope 1. With the learning model 522, it is possible to output the manipulation information with high accuracy in accordance with each operation stage.

Second Embodiment

Figure 7:
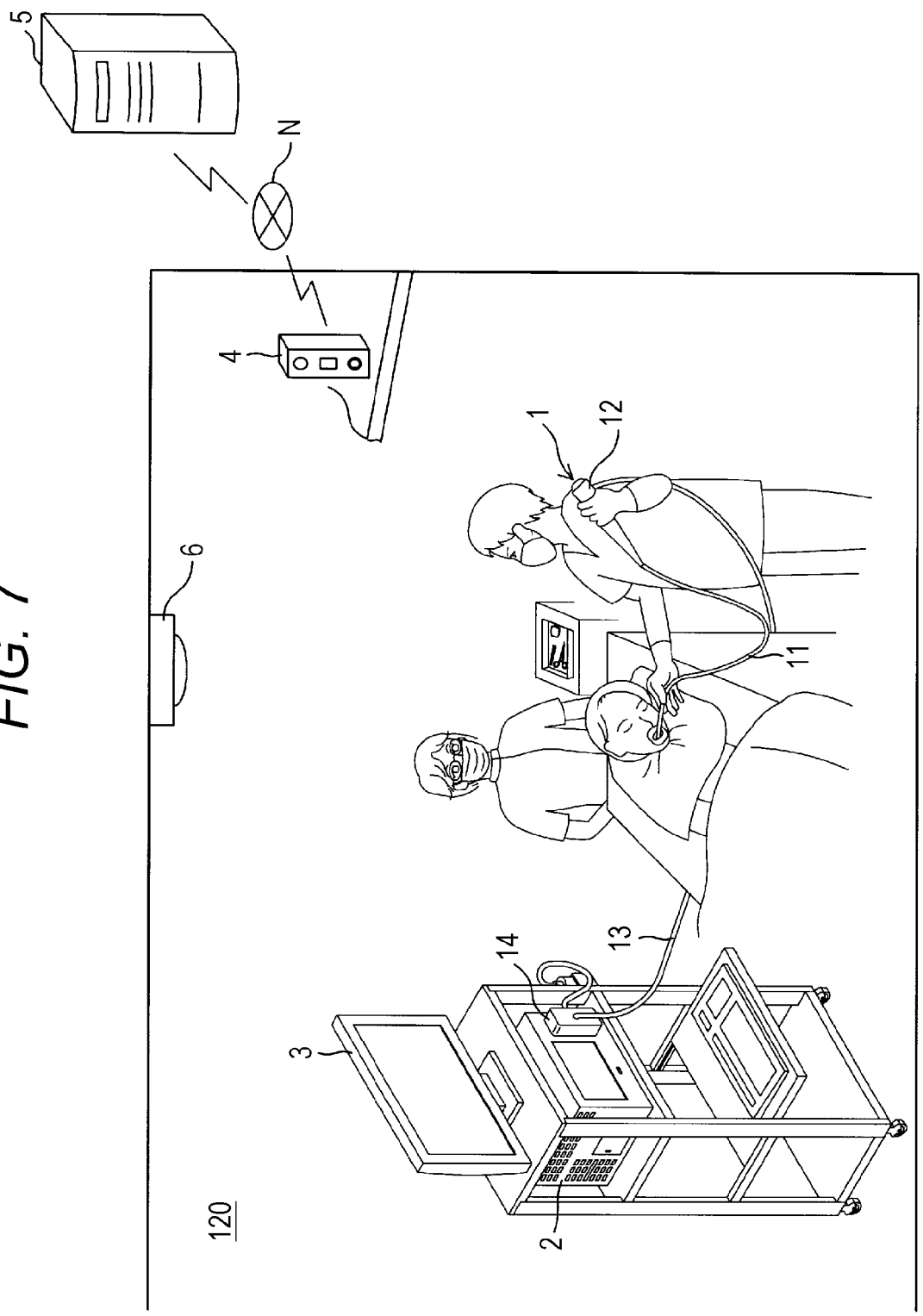
FIG. 7 is a schematic view of a learning model generation system according to a second embodiment.

In a second embodiment, a learning model generation system 120 further includes the imaging device 6 that images an inside of an endoscope room in which the manipulation of the endoscope 1 is performed, and the learning model 522 using an indoor image captured by the imaging device 6 is generated. FIG. 7 is a schematic view of the learning model generation system 120 according to the second embodiment. Hereinafter, a difference between the second embodiment and the first embodiment will be described. Since the other configurations except configurations to be described later are similar to those of the first embodiment, the same reference numerals are given to the common configurations, and the detailed description thereof will be omitted.

The imaging device 6 is an imaging device having an imaging function, such as a camera, installed in the endoscope room including the endoscope operator who operates the endoscope 1 and the subject of the endoscope 1. The imaging device 6 is communicatively connected to the information processing device 5 via the network N in a wired or wireless manner. The imaging device 6 transmits the captured indoor image to the information processing device 5. The indoor image captured by the imaging device 6 includes images indicating various states in the endoscope room, for example, the endoscope operator, the subject, and an assistant such as a nurse assisting the endoscope operator in the endoscope room, and a placing table of the treatment tool in the endoscope room.

Figure 8:
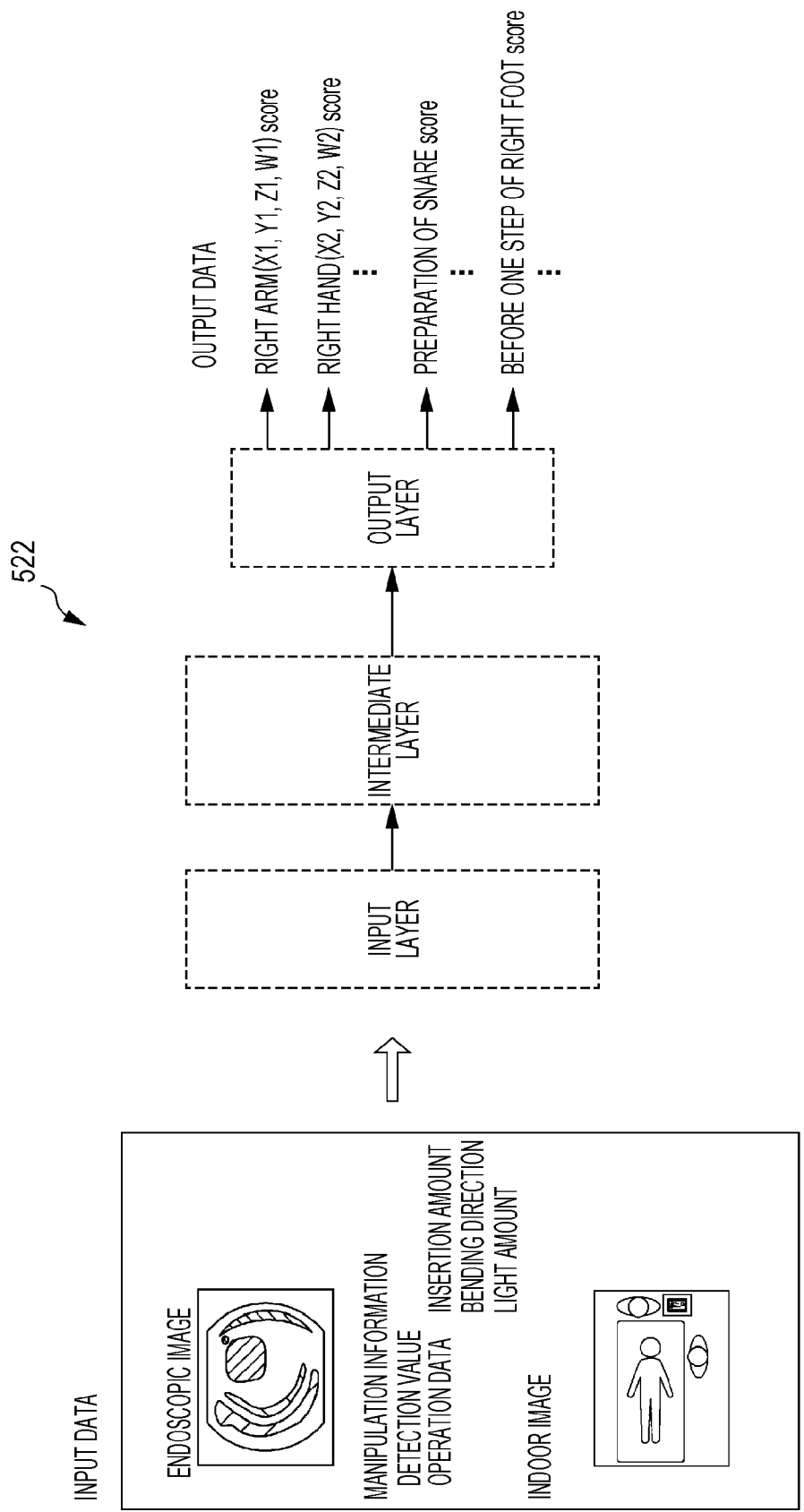
FIG. 8 is an explanatory diagram for explaining a configuration of a learning model of a second embodiment.

FIG. 8 is an explanatory diagram for explaining a configuration of the learning model 522 of the second embodiment. In a case where the endoscopic image, the manipulation information, and the indoor image are input, the learning model 522 is learned so as to output the manipulation information of the next stage. The input data input to the input layer of the learning model 522 are the endoscopic image captured by the endoscope 1, the manipulation information, and the indoor image in a predetermined stage. The manipulation information may include, for example, at least one of the operation data such as the detection value of the detection device 4, the insertion amount, bending direction, and light amount of the endoscope 1. Indoor image data includes information such as relative position information of the endoscope operator and the subject, a direction of the body of the subject, and a preparation state of the treatment tool. Note that in this case, the image data of the endoscopic image and the image data of the indoor image may be input to the input layer via the convolution layer and a convolution layer (not illustrated).

Output data output from the output layer of the learning model 522 is manipulation information of the next stage for the manipulation being performed in a predetermined stage. The manipulation information includes the state data of both hands, both arms, and the like of the endoscope operator. The manipulation information may include information regarding the treatment tool of the next stage (for example, preparation of a snare, preparation of an electric scalpel, and the like), information regarding a positional relationship between the endoscope operator and the subject of the next stage (for example, before one step of the right foot, one step of the both feet to left, and the like), and the like.

The information processing device 5 generates training data in which the endoscopic image, the manipulation information, and the indoor image in each operation stage are labeled with the manipulation information in the next stage of each operation stage, and generates the learning model 522 that outputs the manipulation information of the next stage in a case where the endoscopic image, the manipulation information, and the indoor image are input, by using the generated training data.

According to the present embodiment, the learning model 522 can output the manipulation information more corresponding to performance contents by using the indoor image acquired by the imaging device 6. Since the manipulation information corresponding to the indoor situation is output, it is possible to support not only the endoscope operator but also other assistants and the like.

Third Embodiment

Figure 9:
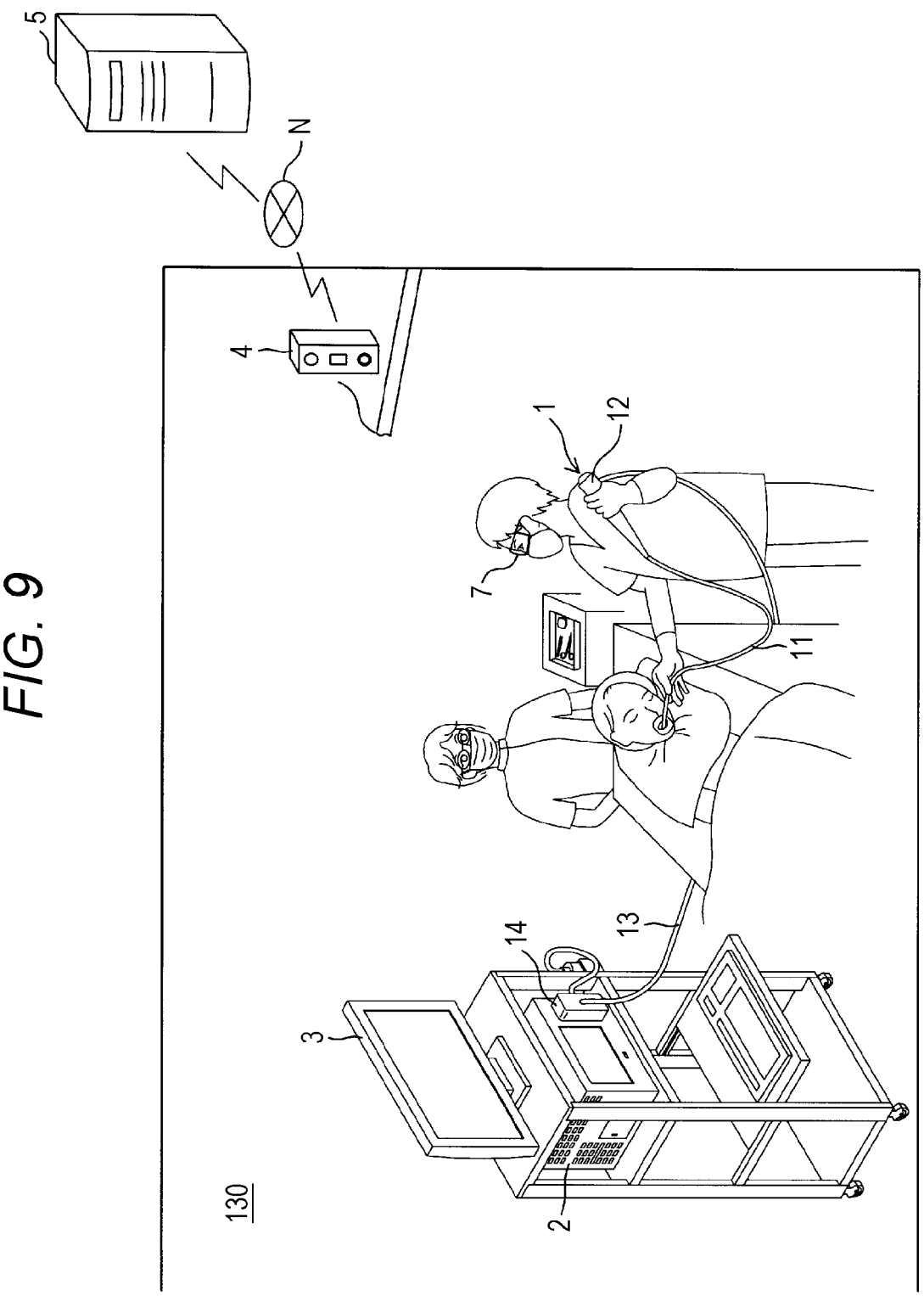
FIG. 9 is a schematic view of a learning model generation system according to a third embodiment.

In a third embodiment, a learning model generation system 130 further includes a visual line detection device 7 that detects visual line data of the endoscope operator, and the learning model 522 using the visual line data detected by the visual line detection device 7 is generated. FIG. 9 is a schematic view of the learning model generation system 130 according to the third embodiment. Hereinafter, a difference between the third embodiment and the first embodiment will be described. Since the other configurations except configurations to be described later are similar to those of the first embodiment, the same reference numerals are given to the common configurations, and the detailed description thereof will be omitted.

The visual line detection device 7 is, for example, a detection device having a visual line detection sensor such as an image sensor. The visual line detection device 7 may have a form of a glasses type wearable device. The visual line detection device 7 detects movement of a visual line of the endoscope operator. The visual line detection device 7 is communicatively connected to the information processing device 5 via the network N in a wired or wireless manner. The visual line detection device 7 transmits the detected visual line data to the information processing device 5.

Figure 10:
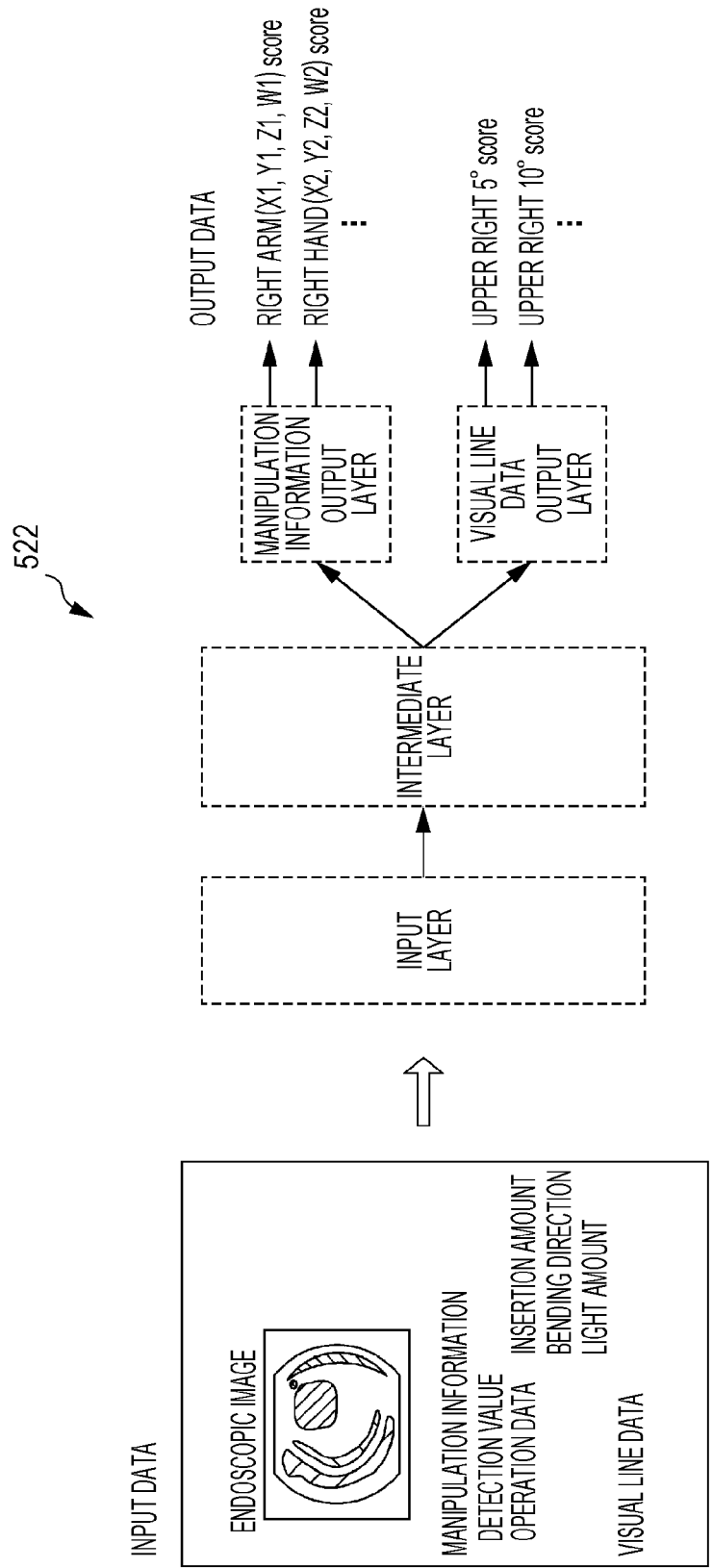
FIG. 10 is an explanatory diagram for explaining a configuration of a learning model of a third embodiment.

FIG. 10 is an explanatory diagram for explaining a configuration of the learning model 522 of the third embodiment. The input data input to the input layer of the learning model 522 are the endoscopic image captured by the endoscope 1, the manipulation information, and the visual line data acquired from the visual line detection device 7 in a predetermined stage. The manipulation information may include, for example, at least one of the operation data such as the detection value of the detection device 4, the insertion amount, bending direction, and light amount of the endoscope 1.

The learning model 522 includes, for example, a plurality of the output layers that output the manipulation information and the visual line data. The output data output from each of the output layers are the manipulation information and visual line data of the next stage for the manipulation being performed in a predetermined stage.

The information processing device 5 generates training data in which the endoscopic image, the manipulation information, and the visual line data in each operation stage are labeled with the manipulation information and the visual line data in the next stage of each operation stage, and generates the learning model 522 that outputs the manipulation information and the visual line data in the next stage in a case where the endoscopic image, the manipulation information, and the visual line data are input, by using the generated training data.

According to the present embodiment, the learning model 522 can output delicate movement as easily recognizable information by converting the movement into data such as the visual line data.

Fourth Embodiment

Figure 11:
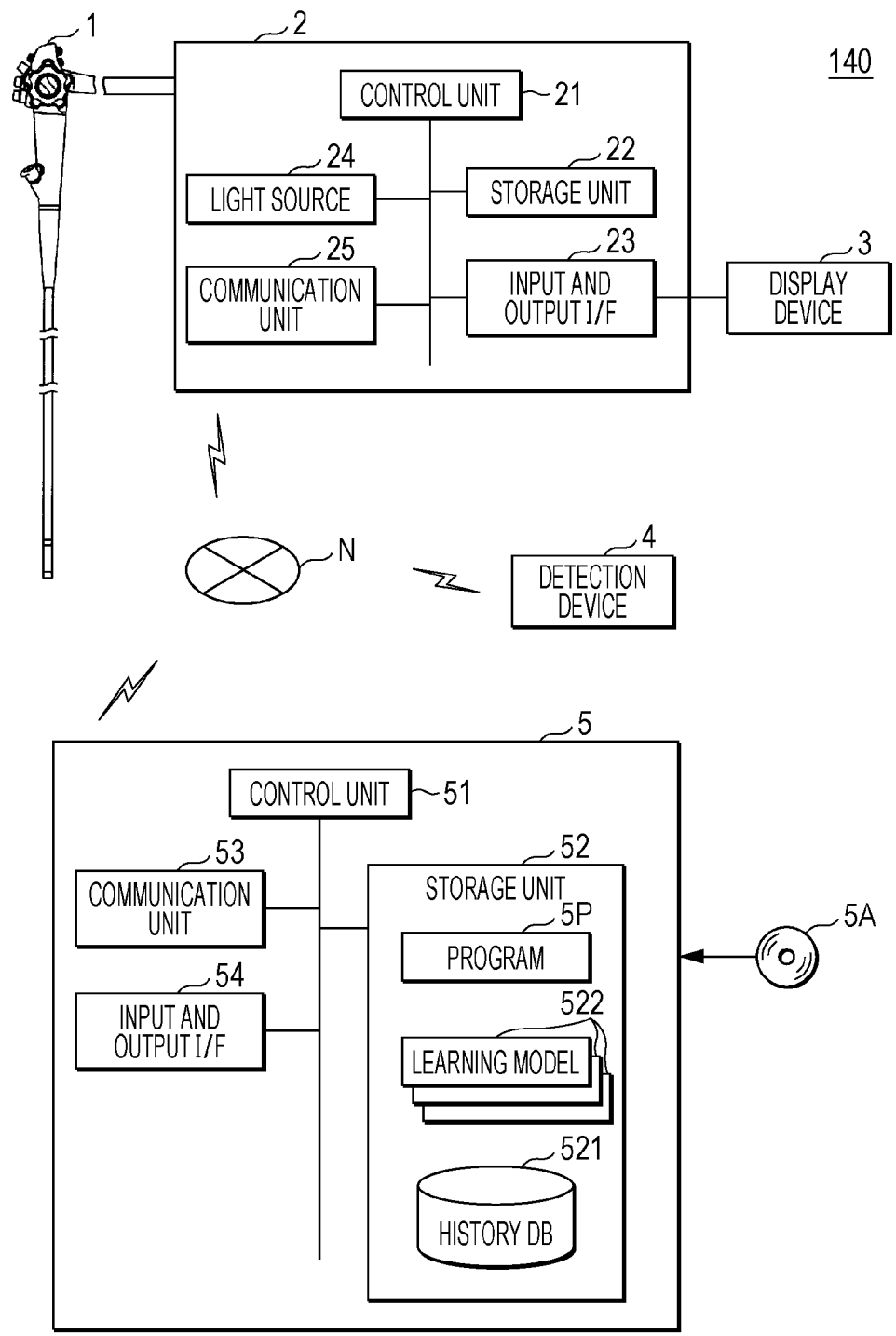
FIG. 11 is a block diagram illustrating a configuration example of a learning model generation system according to a fourth embodiment.

In a fourth embodiment, the information processing device 5 of a learning model generation system 140 generates a plurality of types of learning models 522 corresponding to the manipulation level. FIG. 11 is a block diagram illustrating a configuration example of the learning model generation system 140 according to the fourth embodiment. Hereinafter, a difference between the fourth embodiment and the first embodiment will be described. Since the other configurations except configurations to be described later are similar to those of the first embodiment, the same reference numerals are given to the common configurations, and the detailed description thereof will be omitted. In the information processing device 5 of the fourth embodiment, a plurality of the learning models 522 are stored in the storage unit 52.

As the endoscope operator of the endoscope 1, endoscope operators at various manipulation levels from an endoscope operator who is unskilled in operating the endoscope 1 to an endoscope operator who is skilled in operating the endoscope 1 are assumed. In such a case, it is preferable that different manipulation information is provided according to the manipulation level of the endo scope operator. The learning model generation system 140 outputs the manipulation information corresponding to the manipulation level of the endoscope operator by generating a plurality of the learning models 522 corresponding to the manipulation level.

The learning model 522 is generated for each of different manipulation levels such as a manipulation level for a beginner, a manipulation level for a person with an intermediate level, a manipulation level for a person with an advanced level, and a manipulation level for an expert, and is configured such that only information corresponding to each manipulation level is output as output data from each of the learning models 522. For example, the state data, the operation data including all of the insertion amount, the bending direction, and the light amount, and the like are output from the learning model 522 for a beginner, and only the operation data including the light amount is output as the manipulation information from the learning model 522 for an expert. In this case, each of the learning models 522 may use only the information corresponding to the output data as an input element. That is, in the learning model 522 for an expert, which outputs the light amount as the manipulation information, the manipulation information included in the input element may be only the light amount, and other operation data and state data may not be included in the input element. Note that the learning model generation system 140 may output the output data corresponding to the manipulation level by one learning model 522 by performing learning including the manipulation level of the endoscope operator as the input element of the learning model 522.

Note that a plurality of types of learning models 522 may be prepared based on elements other than the manipulation level. For example, the information processing device 5 may generate a plurality of types of the learning models 522 in accordance with biological attribute information of the endoscope operator.

The endoscope operator of the endoscope 1 has various biological attribute information such as height, weight, gender, a size of a hand, grip strength, a dominant hand, eyesight, and color vision characteristics. For example, a bending operation of the endoscope differs depending on the height of the endoscope operator, the size of the hand, and the like. Furthermore, appropriate light amount and image quality setting differ depending on the eyesight, the color vision characteristics, and the like. In such a case, it is preferable that different manipulation information is provided according to the biological attribute information of the endoscope operator. For example, a plurality of types of the learning models 522 are generated for each body type classification of different endoscope operators in accordance with the body type classified based on the height, the weight, the gender, and the like of the biological attribute information. For example, the learning model 522 corresponding to each body type classified into "large", "medium", and "small" is configured to output the manipulation information corresponding to each of the body types of "large", "medium", and "small". Note that the learning model generation system 140 may output the output data corresponding to the biological attribute information by one learning model 522 by performing learning including the biological attribute information of the endoscope operator as the input element of the learning model 522.

According to the present embodiment, the learning model 522 can output appropriate manipulation information to each operator in accordance with the manipulation level, biological attribute information, and the like of the endoscope operator.

Fifth Embodiment

Figure 12:
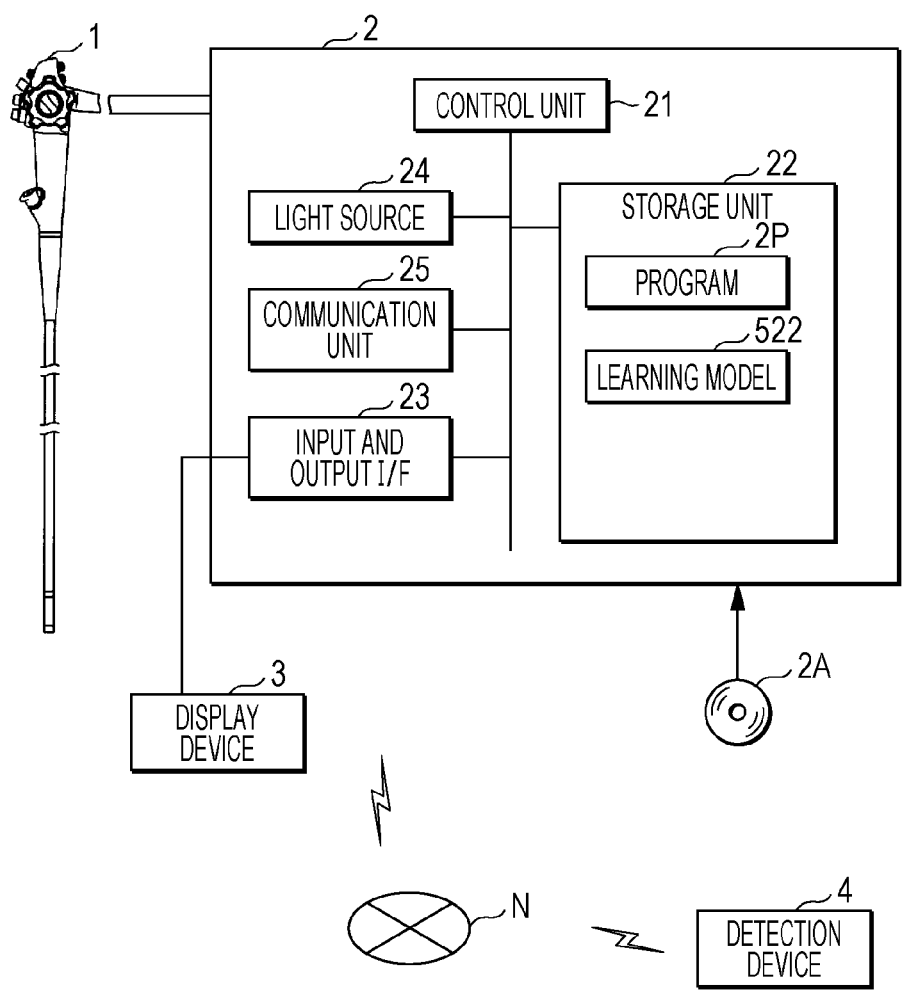
FIG. 12 is a block diagram illustrating a configuration example of a manipulation support system according to a fifth embodiment.

In a fifth embodiment, the processor 2 for an endoscope realizes a manipulation support system that provides the endoscope operator operating the endoscope 1 with the manipulation information by using the learning model 522 generated by the learning model generation system. FIG. 12 is a block diagram illustrating a configuration example of a manipulation support system 210 according to the fifth embodiment. Hereinafter, a difference between the fifth embodiment and the first embodiment will be described. Since the other configurations except configurations to be described later are similar to the learning model generation system 110 of the first embodiment, the same reference numerals are given to the common configurations, and the detailed description thereof will be omitted.

The manipulation support system 210 of the fifth embodiment includes the endoscope 1, the processor 2 for an endoscope, and the detection device 4. A display device 3 is connected to the processor 2 for an endoscope. The processor 2 for an endoscope is communicatively connected to the detection device 4 via the network N in a wired or wireless manner.

The processor 2 for an endoscope according to the fifth embodiment stores a program 2P and the learning model 522 in the storage unit 22, and also stores other programs and data to be referred to by the control unit 21. The program 2P stored in the storage unit 22 may be a program read from a recording medium 2A capable of being read by the processor 2 for an endoscope. Furthermore, the program 2P may be a program downloaded from an external computer (not illustrated) connected to a communication network (not illustrated), and be stored in the storage unit 22.

The control unit 21 reads and executes the program 2P stored in the storage unit 22 to acquire the endoscopic image, the manipulation information of the endoscope operator, and the like, and functions as the processor 2 for an endoscope peculiar to the present disclosure which outputs the manipulation information of the next stage which corresponds to the acquired endoscopic image and the acquired manipulation information of the endoscopic operator.

Figure 13:
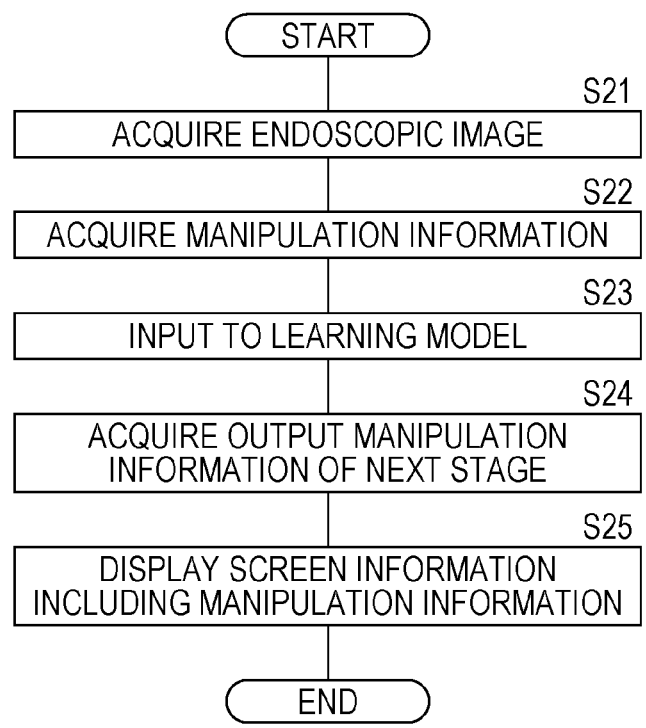
FIG. 13 is a flowchart illustrating an example of a processing procedure performed by a processor for an endoscope.

FIG. 13 is a flowchart illustrating an example of a processing procedure performed by the processor 2 for an endoscope. For example, when an operation manipulation of the endoscope 1 is started by the endoscope operator and imaging of the endoscope 1 is started, the following processing is executed by the control unit 21 of the processor 2 for an endoscope.

The control unit 21 acquires a captured image from the endoscope 1, and acquires an endoscopic image obtained by performing predetermined image processing on the acquired captured image (step S21). Next, the control unit 21 acquires the manipulation information (step S22). The manipulation information includes at least any one of the state data such as both hands and both arms of the endoscope operator or the operation data such as the insertion amount, bending direction, and light amount of the endoscope 1. Specifically, the control unit 21 acquires the detection value detected by the detection device 4. The control unit 21 calculates the coordinate value for each part of the endoscope operator from the 3D data group acquired from the detection device 4. Moreover, the control unit 21 acquires the operation data such as the insertion amount, bending direction, and light amount of the endoscope 1. The control unit 21 temporarily stores the acquired endoscopic image and the acquired manipulation information in the storage unit 22.

The control unit 21 inputs the stored endoscopic image and the stored manipulation information to the learning model 522 (step S23). The learning model 522 is the learning model 522 described in the first embodiment, and outputs the manipulation information of the next stage in a case where the endoscopic image and the manipulation information are input. Specifically, in a case where the endoscopic image and the state data such as both hands, both arms, and the like of the endoscope operator are input, the learning model 522 outputs the state data such as both hands, both arms, and the like of the next stage or an image generated based on the state data. The learning model 522 may output the operation data of the next stage in a case where the endoscopic image and the operation data such as the insertion amount, bending direction, and light amount of the endoscope 1 are input.

The endoscopic image input to the learning model 522 may be the captured image itself captured by the image sensor provided in the endoscope 1 and transmitted to the processor 2 for an endoscope, or may be an endoscopic image obtained by performing predetermined image processing on the captured image in the processor 2 for an endoscope. The manipulation information input to the learning model 522 includes at least any one of the state data such as both hands and both arms of the endoscope operator or the operation data such as the insertion amount, bending direction, and light amount of the endoscope 1.

The control unit 21 acquires the manipulation information of the next stage, which is output from the learning model 522 (step S24). The manipulation information output from the learning model 522 includes at least any one of the state data such as both hands and both arms of the endoscope operator in the next stage or the operation data such as the insertion amount, bending direction, and light amount of the endoscope 1. The manipulation information output from the learning model 522 may be an image based on the state data such as both hands and both arms of the endoscope operator.

The control unit 21 generates screen information for displaying the acquired manipulation information and the acquired endoscopic image in association with each other. The control unit 21 displays the screen information including the generated manipulation information by using the display device 3 (step S25), and ends a series of processing. Note that after executing the processing of step S25, the control unit 21 may perform a loop processing to execute the processing of step S21 again.

In the present embodiment, a part of the processing executed by the processor 2 for an endoscope may be performed by the information processing device 5 of the first embodiment or another external server which is communicatively connected to the processor 2 for an endoscope.

Figure 14:
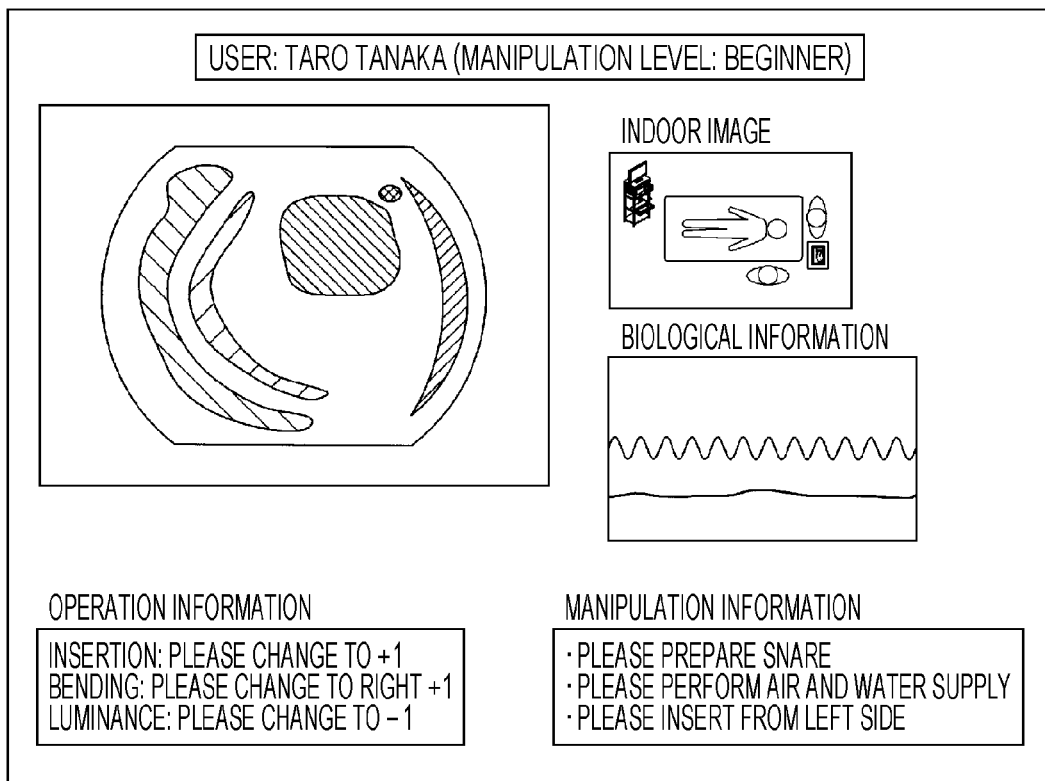
FIG. 14 is a diagram illustrating an example of a screen displayed on a display device.

FIG. 14 is a diagram illustrating an example of a screen displayed on the display device 3. The endoscopic image and the manipulation information of the next stage are displayed on the screen. Based on output information of the learning model 522, the control unit 21 of the processor 2 for an endoscope refers to a table (not illustrated) storing display contents of the manipulation information, and generates image information for displaying the manipulation information of the next stage. The control unit 21 displays the endoscopic image of a predetermined stage and the generated image information for displaying the manipulation information of the next stage in association with each other on the display device 3. On the display device 3, for example, information regarding the operation such as the insertion amount and bending direction of the endoscope 1 and information regarding the entire manipulation such as other air supply and water supply are displayed in parallel as the manipulation information of the next stage. The change amount of the insertion amount may be displayed as "+1 (inserted by 1 cm)", "−1 (removed by 1 cm)", "0 (current state is maintained)", or the like. In a case where the manipulation information with the image is output from the learning model 522, a screen including the image may be displayed. In a case where the manipulation information of a plurality of stages including the subsequent stages and the like is acquired from the learning model 522, the information of a plurality of the stages may be displayed in parallel.

In a case where the indoor image, the visual line data, and the like are acquired, the control unit 21 may display a screen including these image data. Moreover, the control unit 21 may acquire biological information such as a blood pressure and a heartbeat of the subject from an external measurement device communicatively connected to the processor 2 for an endoscope and display the biological information together with the manipulation information on the screen. By aggregating various pieces of information and displaying the information on the display device 3, the endoscope operator can obtain information without moving the visual line to a plurality of monitors, and is prevented from overlooking the information.

In addition to outputting the screen information, the control unit 21 may notify the operator of the manipulation information by using a warning sound, a synthetic voice, blinking of a screen, or the like. For example, in a case where the manipulation information requiring attention is included in the output information, for example, in a case where the operation amount in the bending direction of the next stage is equal to or greater than a preset threshold, it is preferable to notify the operator of the manipulation information by using the warning sound, the synthetic voice, or the like via a speaker (not illustrated). Furthermore, in a case where the manipulation information includes setting information for the processor 2 for an endoscope, for example, a change instruction may be output to the processor 2 for an endoscope instead of the output to the display device 3 or in addition to the output to the display device 3. For example, changes related to the setting of the processor 2 for an endoscope, such as luminance change of the light source 24 and an image quality parameter change are automatically performed by the processor 2 for an endoscope, and thus the burden of the endoscope operator can be reduced.

According to the present embodiment, the manipulation information corresponding to the manipulation contents performed by the endoscope operator is provided by using the learning model 522. Since the manipulation information of the next stage, which is estimated based on the manipulation data of the skilled endoscope operator, is provided, it is possible to prevent an erroneous manipulation from being performed, and even an endoscope operator who is not skilled in the manipulation can perform the same manipulation contents as that of the skilled endoscope operator. By using the learning model 522, the processor 2 for an endoscope outputs the manipulation information of the next stage, which includes the delicate motion of the fingers peculiar to the endoscope 1, based on the information regarding the manipulation in the operation stage acquired at high speed and with high accuracy by using the endoscopic image, the detection value of the detection device 4, and the like.

Sixth Embodiment

In a sixth embodiment, a manipulation support system 220 is different from that of the fifth embodiment in that the imaging device 6 is further provided which images the inside of the endoscope room in which the endoscope 1 is operated. In a case where the endoscopic image, the manipulation information, and the indoor image are input, the processor 2 for an endoscope provides the manipulation information by using the learning model 522 learned so as to output the manipulation information of the next stage.

Figure 15:
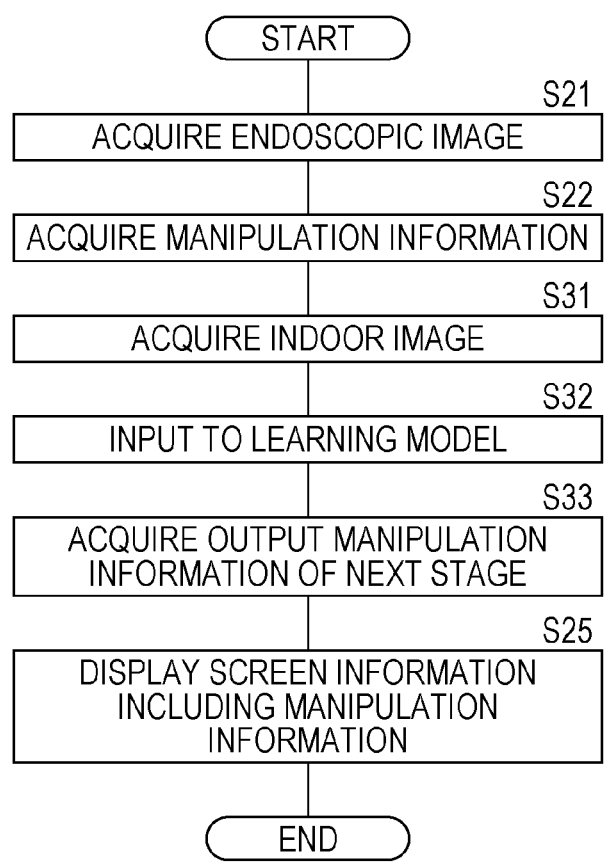
FIG. 15 is a flowchart illustrating an example of a processing procedure performed by a processor for an endoscope according to a sixth embodiment.

FIG. 15 is a flowchart illustrating an example of a processing procedure performed by the processor 2 for an endoscope according to the sixth embodiment. Processing common to those in FIG. 13 of the fifth embodiment are denoted by the same step numbers, and detailed descriptions thereof will be omitted.

The control unit 21 acquires the endoscopic image (step S21) and acquires the manipulation information (step S22). The manipulation information includes at least any one of the state data such as both hands and both arms of the operator or the operation data such as the insertion amount, bending direction, and light amount of the endoscope 1. Next, the control unit 21 acquires the indoor image from the imaging device 6 (step S31). The control unit 21 temporarily stores the acquired endoscopic image, the acquired manipulation information, and the acquired indoor image in the storage unit 22.

The control unit 21 inputs the stored endoscopic image, the stored manipulation information, and the stored indoor image to the learning model 522 (step S32). The learning model 522 is the learning model 522 described in the second embodiment, and outputs the manipulation information of the next stage in a case where the endoscopic image, the manipulation information, and the indoor image are input. The control unit 21 acquires the manipulation information of the next stage output from the learning model 522 (step S33). The control unit 21 generates screen information for displaying the acquired manipulation information and the acquired endoscopic image in association with each other. The control unit 21 displays the screen information including the generated manipulation information by using the display device 3 (step S25), and ends a series of processing.

The screen displayed on the display device 3 includes regions such as the endoscopic image, the operation information of the next stage, the indoor image, and the biological information. The operation information of the next stage includes, for example, the state data of both hands and both arms of the endoscope operator, motion information based on a positional relationship between the endoscope operator and the subject, information regarding the treatment tool, and the like.

Seventh Embodiment

In a seventh embodiment, a manipulation support system 230 is different from that of the fifth embodiment in that the visual line detection device 7 that detects the visual line data of the endoscope operator is further provided. In a case where the endoscopic image, the manipulation information, and the visual line data are input, the processor 2 for an endoscope provides the manipulation information by using the learning model 522 learned so as to output the manipulation information and visual line data of the next stage.

Figure 16:
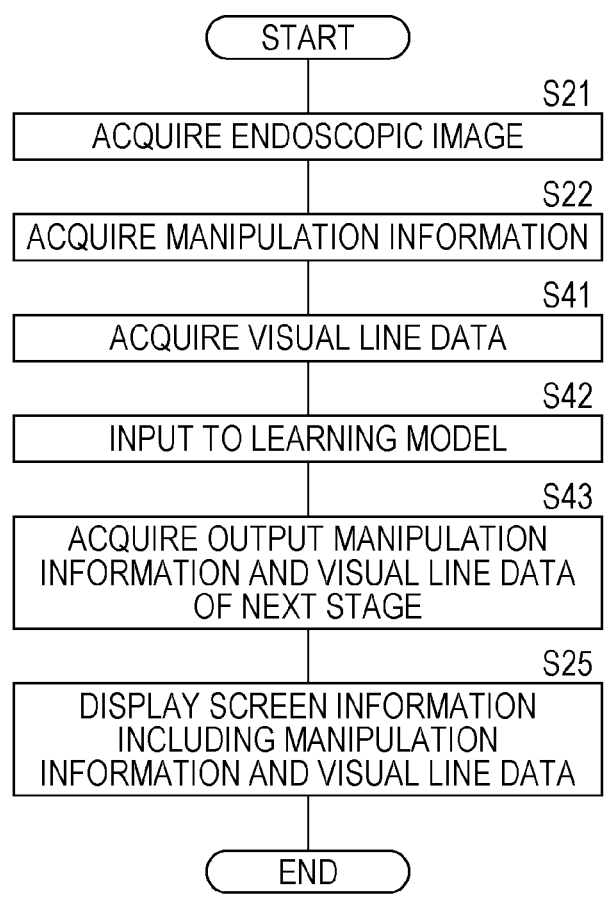
FIG. 16 is a flowchart illustrating an example of a processing procedure performed by a processor for an endoscope according to a seventh embodiment.

FIG. 16 is a flowchart illustrating an example of a processing procedure performed by the processor 2 for an endoscope according to the seventh embodiment. Processing common to those in FIG. 13 of the fifth embodiment are denoted by the same step numbers, and detailed descriptions thereof will be omitted.

The control unit 21 acquires the endoscopic image (step S21) and acquires the manipulation information (step S22). The manipulation information includes at least any one of the state data such as both hands and both arms of the operator or the operation data such as the insertion amount, bending direction, and light amount of the endoscope 1. Next, the control unit 21 acquires the visual line data from the visual line detection device 7 (step S41). The control unit 21 temporarily stores the acquired endoscopic image, the acquired manipulation information, and the acquired visual line data in the storage unit 22.

The control unit 21 inputs the stored endoscopic image, the stored manipulation information, and the stored visual line data to the learning model 522 (step S42). The learning model 522 is the learning model 522 described in the third embodiment, and outputs the manipulation information and visual line data of the next stage in a case where the endoscopic image, the manipulation information, and the visual line data are input. The control unit 21 acquires the manipulation information and visual line data of the next stage, which are output from the learning model 522 (step S43). The control unit 21 generates screen information for displaying the acquired manipulation information, the acquired visual line data, and the endoscopic image in association with each other. The control unit 21 displays the screen information including the generated manipulation information and the generated visual line data by using the display device 3 (step S25), and ends a series of processing.

The screen displayed on the display device 3 includes regions such as the endoscopic image, a visual line image, the operation information of the next stage, and the visual line data. Note that the control unit 21 may output the visual line data with the synthetic voice or the like via the speaker (not illustrated). In a case where the endoscope operator wears the visual line detection device 7 including the glasses type wearable device, the control unit 21 may output the visual line data by turning on a part of a lens corresponding to a visual line direction of the next stage or the like.

Eighth Embodiment

An eighth embodiment is different from the fifth embodiment in that the processor 2 for an endoscope of the manipulation support system 240 stores a plurality of types of the learning models 522 in the storage unit. The processor 2 for an endoscope provides the manipulation information by using the learning model 522 specified according to the endoscope operator.

Figure 17:
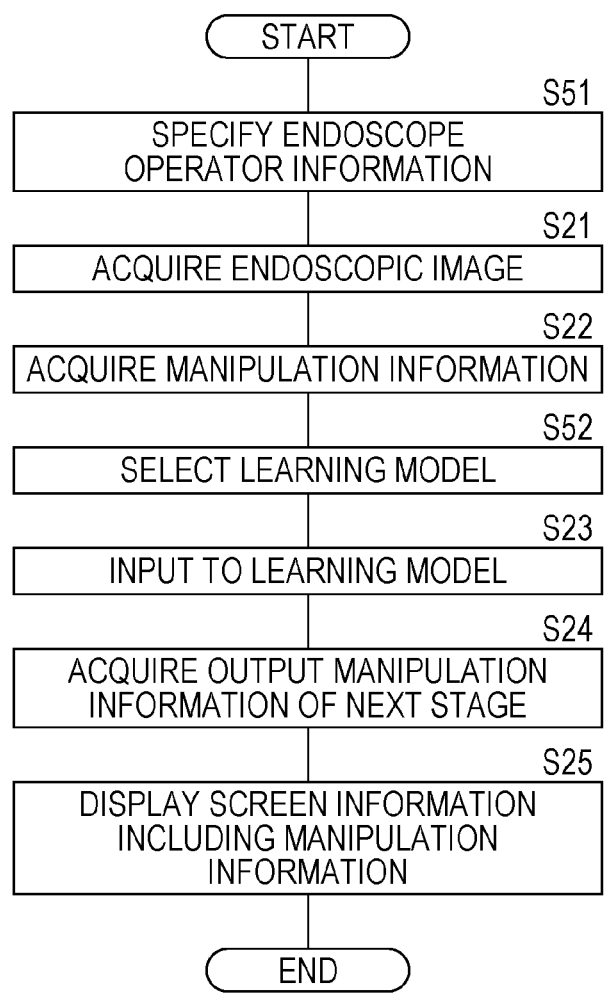
FIG. 17 is a flowchart illustrating an example of a processing procedure performed by a processor for an endoscope according to an eighth embodiment.

FIG. 17 is a flowchart illustrating an example of a processing procedure performed by the processor 2 for an endoscope according to the eighth embodiment. Processing common to those in FIG. 13 of the fifth embodiment are denoted by the same step numbers, and detailed descriptions thereof will be omitted.

For example, the control unit 21 acquires the manipulation level of the endoscope operator by referring to a database (not illustrated) or the like that acquires and stores, in advance, endoscope operator information such as the manipulation level of the endoscope operator of the endoscope 1 and the biological attribute information, and then specifies the manipulation level (endoscope operator information) (step S51). The manipulation level is determined based on, for example, the past operation contents of the endoscope 1 by the endoscope operator and recorded in the database. Note that the processor 2 for an endoscope may receive selective input of the endoscope operator information from the endoscope operator by using the input device such as a touch panel or a keyboard.

The operation of the endoscope 1 is started, and the control unit 21 acquires the endoscopic image (step S21) and acquires the manipulation information (step S22). The control unit 21 temporarily stores the acquired endoscopic image and the acquired manipulation information in the storage unit 22.

The storage unit 22 of the processor 2 for an endoscope stores a plurality of the learning models 522 corresponding to the manipulation level described in the fourth embodiment. The control unit 21 selects the learning model 522 to be used based on the specified manipulation level by referring to the database or the like in which the manipulation level and identification information of each learning model 522 are recorded in advance in association with each other (step S52). The control unit 21 inputs the stored endoscopic image and the stored manipulation information to the selected learning model 522 (step S23), and acquires the manipulation information of the next stage and the like output from the learning model 522 (step S24). Only the manipulation information corresponding to the manipulation level of the endoscope operator is output from the learning model 522. Note that the control unit 21 may input the specified manipulation level as one of the input elements of the learning model 522 and output the manipulation information corresponding to the manipulation level. The control unit 21 generates screen information for displaying the acquired manipulation information and the acquired endoscopic image in association with each other. The control unit 21 displays the screen information including the generated manipulation information by using the display device 3 (step S25), and ends a series of processing.

In the above description, the processor 2 for an endoscope may use a plurality of types of the learning models 522 different in accordance with the biological attribute information. In step S51, the control unit 21 acquires the biological attribute information such as the height and weight of the endoscope operator instead of the manipulation level of the endoscope operator, and specifies the body type (endoscope operator information) of the endoscope operator. In step S52, the control unit 21 selects the learning model 522 to be used based on the specified body type of the endoscope operator by referring to the database or the like in which the body type and the identification information of the learning model 522 are recorded in advance in association with each other. The manipulation information corresponding to the body type of the endoscope operator is output from the learning model 522.

Note that, in a case where the manipulation level of the endoscope operator is not registered in the database, for example, in a case where the endoscope operator manipulates the endoscope 1 for the first time, a temporary level may be specified by general-purpose setting based on attribute information other than the manipulation level of the endoscope operator. For example, based on the years of experience of the endoscope operator, the beginner level may be applied in a general-purpose manner in a case where the endoscope operator has experience of less than one year, the intermediate level is applied in a general-purpose manner in a case where the endoscope operator has the experience of one year or more and less than five years. Furthermore, an endoscope operator including the biological attribute information most approximate to the biological attribute information of a target endoscope operator may be derived based on the biological attribute information of the target endoscope operator, and the manipulation level of the derived endoscope operator may be applied as the temporary level. Moreover, before the start of the manipulation, for example, a manipulation using a simulation device such as a large intestine model may be performed to derive a virtual manipulation level, and the derived virtual manipulation level may be applied as the temporary level.

According to the present embodiment, the manipulation information is output by using the learning model 522 adjusted so as to output only information corresponding to the manipulation level or the biological attribute information of the endoscope operator specified by the processor 2 for an endoscope. Since the manipulation information suitable for each endoscope operator is provided, even endoscope operators having various manipulation levels, or biological attributes can provide highly useful support information.

Ninth Embodiment

Figure 18:
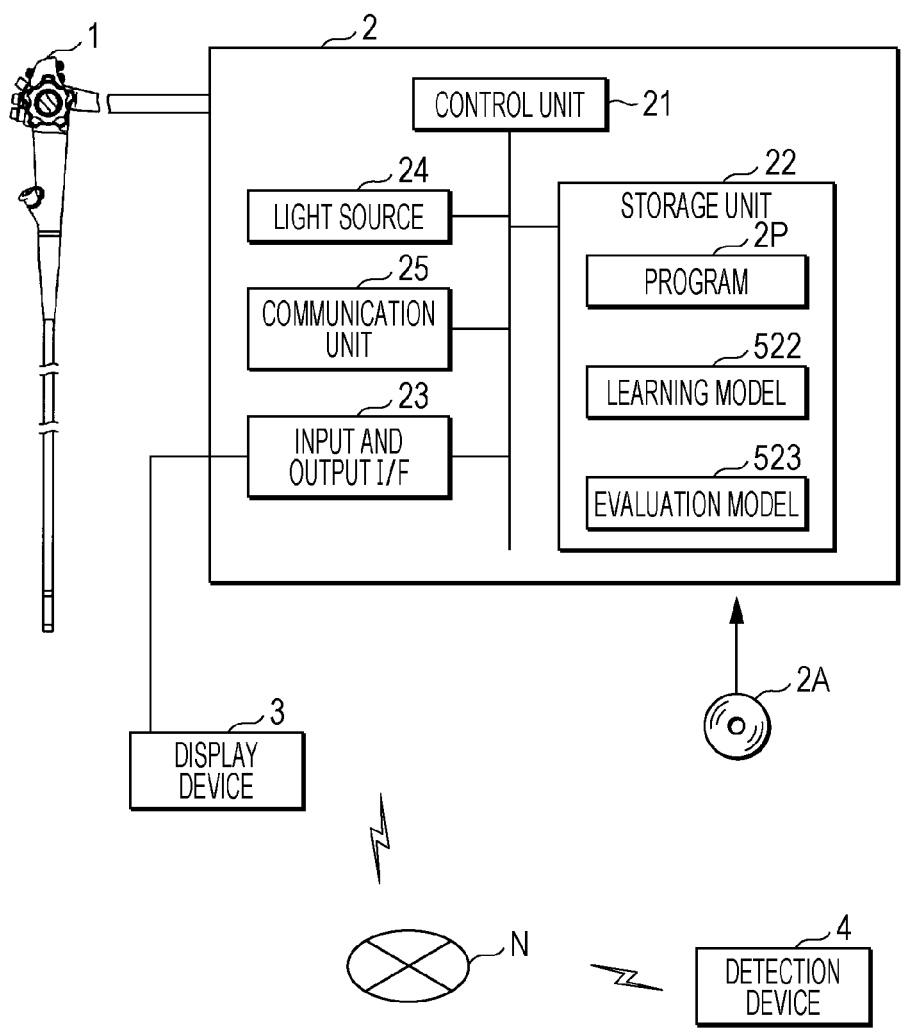
FIG. 18 is a block diagram illustrating a configuration example of a manipulation support system according to a ninth embodiment.

In a ninth embodiment, the processor 2 for an endoscope of a manipulation support system 250 evaluates the manipulation level of the endoscope operator by using an evaluation model 523 for evaluating the manipulation level of the endoscope operator. FIG. 18 is a block diagram illustrating a configuration example of the manipulation support system 250 according to the ninth embodiment. Hereinafter, a difference between the ninth embodiment and the fifth embodiment will be described. Since the other configurations except configurations to be described later are similar to those of the fifth embodiment, the same reference numerals are given to the common configurations, and the detailed description thereof will be omitted.

The storage unit 22 of the processor 2 for an endoscope further stores the evaluation model 523. The evaluation model 523 is an evaluator that evaluates the manipulation level of the endoscope operator, and is a learning model generated by machine learning.

Figure 19:
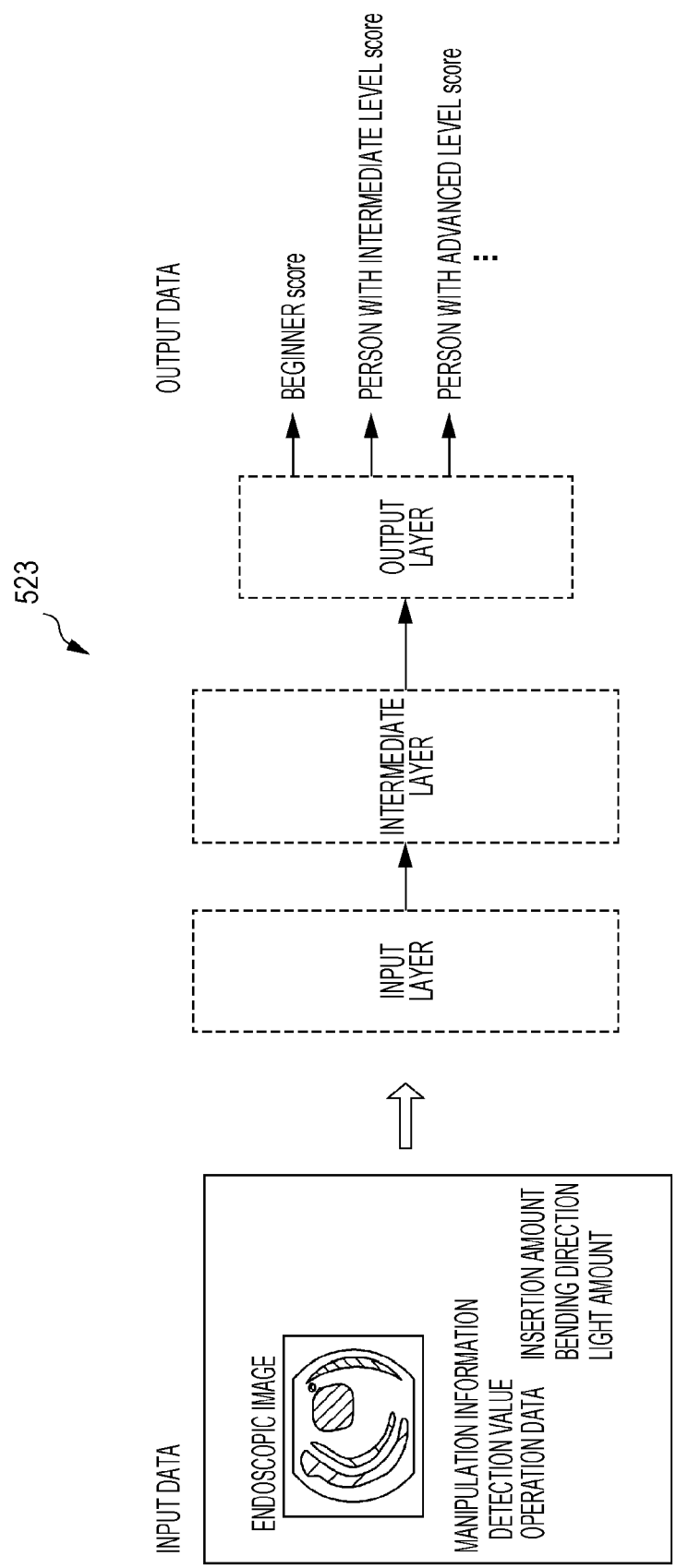
FIG. 19 is an explanatory diagram for explaining a configuration of an evaluation model.

FIG. 19 is an explanatory diagram for explaining a configuration of the evaluation model 523. The evaluation model 523 is generated and learned by deep learning using the neural network. In the example illustrated in FIG. 19, the evaluation model 523 includes an input layer that inputs endoscopic image data and manipulation information, an output layer that outputs an ability level, and an intermediate layer that extracts feature amounts of the endoscopic image data and the manipulation information. The intermediate layer includes a plurality of nodes that extract the feature amounts of the endoscopic image data and manipulation information, and passes image feature amounts extracted by using various parameters to the output layer. The intermediate layer may include a convolution layer, a pooling layer, and the like. The evaluation model 523 includes the output layer including channels each corresponding to the set manipulation level, and the output layer outputs accuracy for each manipulation level as a score.

The input data to the evaluation model 523 are the endoscopic image captured by the endoscope 1 and the manipulation information. The manipulation information may include the detection value indicating the state data such as both hands and both arms of the endoscope operator, and the operation data such as the insertion amount, bending direction, and light amount of the endoscope 1. The input data may further include an indoor image, visual line data, and the like. Note that in this case, image information may be input to the input layer via the convolution layer and a convolution layer (not illustrated). The output data from the evaluation model 523 is the manipulation level of the operator with respect to the endoscopic image data and the manipulation information. The manipulation level is classified into, for example, the beginner, the person with an intermediate level, the person with an advanced level, and the expert.

In the evaluation model 523, model parameters are adjusted by using a training database in which the endoscopic image and manipulation information, and the manipulation level in the endoscopic image and manipulation information are recorded in association with each other. The training data is constructed as a data set in which the manipulation level is labeled with respect to the endoscopic image and the manipulation information. For example, in a large intestine endoscopy, an endoscope operator with a cecal intubation rate of 95% or greater and a cecal intubation time of 5 minutes or less is considered to be the person with an intermediate level. An endoscope operator with a tumor discovery rate of 30% or greater at the time of initial examination is considered as the expert. In a polypectomy or other endoscopic mucosal resection, an endoscope operator who performs resection by supplying power once within a predetermined time is considered to be in a high manipulation level. Furthermore, also in a case where there is no waste in the motion of the arm, the wrist, the finger, and the like during the manipulation, the manipulation level of the endoscope operator is considered to be high. The evaluation model 523 executes learning by using the training data corresponding to these findings.

The evaluation model 523 inputs the endoscopic image data and the manipulation information as input data for learning. The evaluation model 523 is learned so as to output the manipulation level in a case where the endoscopic image data and the manipulation information are input by using the manipulation level for each input data for learning as the training data. As the learning progresses, a learned model parameter is obtained. By applying the learned model parameter to the defined neural network, the evaluation model 523 can output the manipulation level in a case where the endoscopic image data and the manipulation information are input.

Note that the evaluation model 523 is not limited to deep learning using the neural network, and may be a model learned by another algorithm or may derive an evaluation value by a specific mathematical formula.

Figure 20:
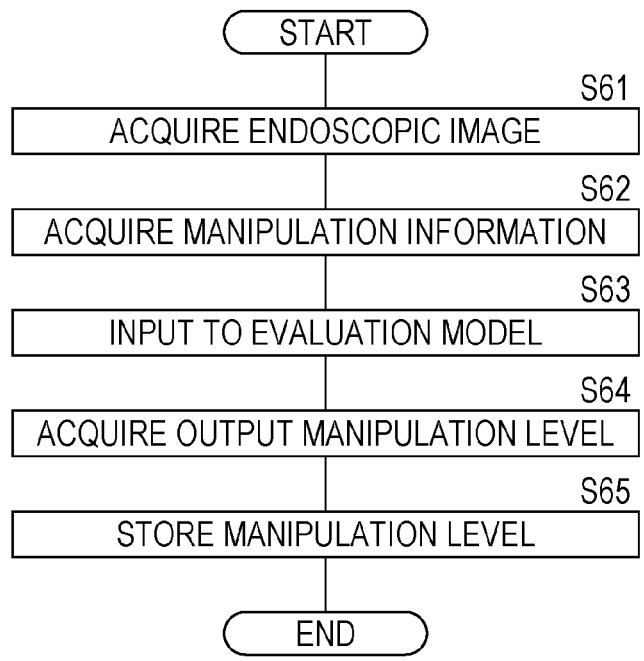
FIG. 20 is a flowchart illustrating an example of a processing procedure performed by a processor for an endoscope.

FIG. 20 is a flowchart illustrating an example of a processing procedure executed by the processor 2 for an endoscope. For example, when the operation manipulation of the endoscope 1 is started by the endoscope operator and imaging of the endoscope 1 is started, the following processing is executed by the control unit 21 of the processor 2 for an endoscope in parallel with estimation processing for the manipulation information.

The control unit 21 acquires the endoscopic image (step S61) and acquires the manipulation information (step S62). The control unit 21 inputs the acquired endoscopic image and the acquired manipulation information to the evaluation model 523 (step S63), and acquires the manipulation level output from the evaluation model 523 (step S64). The control unit 21 stores the acquired manipulation level in association with the endoscope operator in a database or the like storing the endoscope operator information (step S65), and ends a series of the processing.

In a case where the processor 2 for an endoscope stores the learning model 522 corresponding to a plurality of types of the manipulation levels, the control unit 21 may specify the learning model 522 to be used by using the manipulation level evaluated above. Moreover, the control unit 21 may output the manipulation information corresponding to the manipulation level acquired in real time by using the learning model 522 and the evaluation model 523. The control unit 21 executes evaluation processing for the manipulation level and the estimation processing for the manipulation information in parallel at the time of performing the operation of the endoscope 1. The control unit 21 acquires the manipulation level output from the evaluation model 523 in real time, and changes selection of the learning model 522 to be used as needed according to the acquired manipulation level. The control unit 21 acquires the manipulation information output from the selected learning model 522. In this manner, the control unit 21 changes the manipulation information to be output according to the manipulation level of the endoscope operator, which changes based on the performance contents of the manipulation by using the learning model 522 corresponding to the manipulation level of the endoscope operator, which changes during the manipulation.

According to the present embodiment, provision of the manipulation information to the endoscope operator and evaluation for the manipulation level of the endoscope operator are performed in parallel by using the learning model 522 and the evaluation model 523. Since the output contents of the manipulation information can be changed according to the manipulation level evaluated in real time, it is possible to provide appropriate manipulation information in accordance with the performance contents.

Tenth Embodiment

In a tenth embodiment, the processor 2 for an endoscope estimates the manipulation information of the next stage according to a type of the endoscope 1 by using the learning model 522.

The information processing device 5 generates a plurality of types of the learning models 522 corresponding to the type of the endoscope 1. The processor 2 for an endoscope acquires a plurality of types of the learning models 522 corresponding to the type of the endoscope 1 and stores the learning models in the storage unit 52. In each learning model 522, for example, the input data and the output data of the bending direction are different according to the type of the endoscope 1. For example, in the case of an endoscope for an upper gastrointestinal tract or a large intestine endoscope, the operation unit 12 includes a vertical angle knob for bending the distal end of the endoscope 1 in the vertical direction and a horizontal angle knob for bending the distal end of the endoscope 1 in a horizontal direction. Therefore, the bending direction includes operation data for four directions of up, down, right, and left. On the other hand, in the case of an endoscope 1 for bronchi or otolaryngology, the operation unit 12 includes only the vertical angle knob, and the bending direction includes two upper and lower directions. Accordingly, in a case where the type of the endoscope 1 is for bronchi or otolaryngology, the learning model 522 preferably has a configuration in which only operation data for two upper and lower directions as the bending direction is set as input data and only operation data for two upper and lower directions is set as output data.

Note that in a case where the angle knob is configured by a joystick or the like, the bending direction may be indicated by using an operation angle. Furthermore, in the learning model 522 for the endoscope 1 for bronchi or otolaryngology, an entire rotation (twisting) direction and a rotation amount of the insertion tube 11 of the endoscope 1 may be included in the operation data of the manipulation information.

The control unit 21 of the processor 2 for an endoscope specifies the type of the endoscope 1 based on a connector shape of the endoscope 1 connected to the processor 2 for an endoscope, signal information obtained from the endoscope 1, or the like. For example, the control unit 21 may acquire the type of the endoscope 1 by acquiring an identification code of the endoscope 1 via a reading unit (not illustrated), receiving an input from the endoscope operator, or the like. The control unit 21 selects the learning model 522 to be used based on the specified type of the endoscope 1 by referring to the database or the like in which the type of the endoscope 1 and the identification information of each learning model 522 are recorded in association with each other. The control unit 21 inputs the endoscopic image and the manipulation information to the selected learning model 522, and acquires the manipulation information of the next stage and the like output from the learning model 522.

Note that the learning model 522 may include the type of the endoscope 1 as an input element and may output the output data corresponding to the type of the endoscope 1. In this case, the control unit 21 inputs the specified type of the endoscope 1, the endoscopic image, and the manipulation information to the learning model 522, and acquires the manipulation information of the next stage and the like output from the learning model 522. The processor 2 for an endoscope may store only one learning model 522 corresponding to the type of the endoscope 1 scheduled to be connected in the storage unit 52 according to the predetermined type of the endoscope 1 scheduled to be connected.

According to the present embodiment, since the manipulation information corresponding to the type of the endoscope 1 is output, it is possible to provide support information more appropriate for the manipulation state.

Eleventh Embodiment

Figure 21:
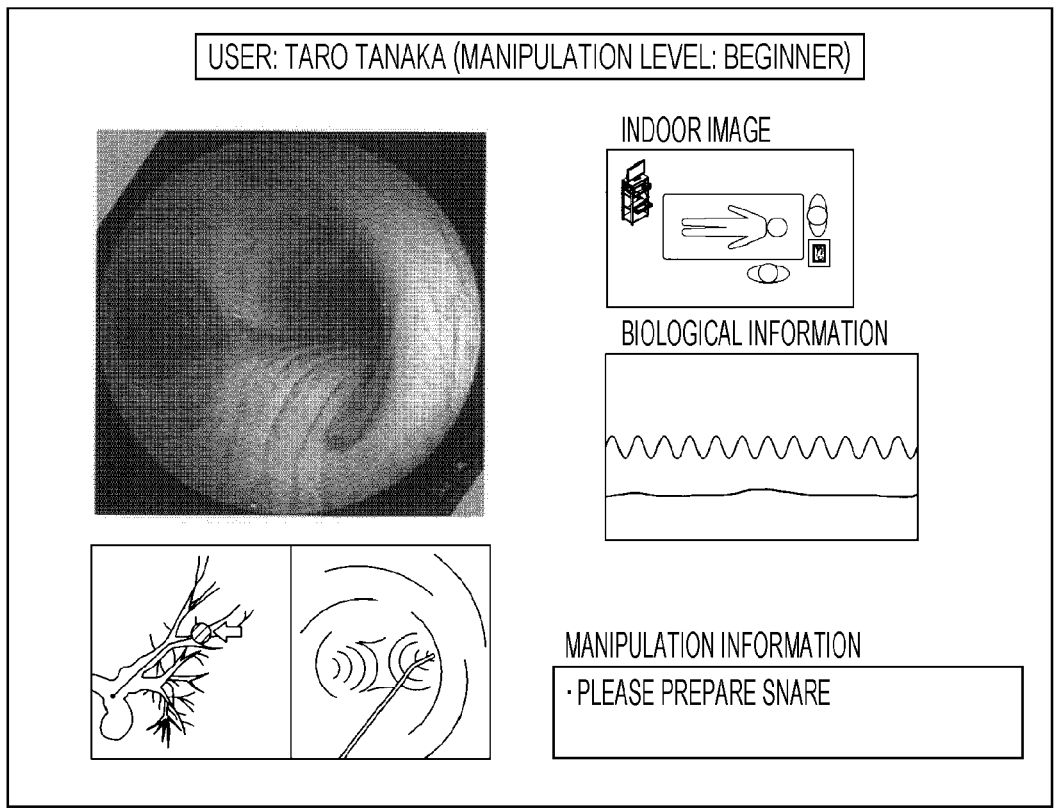
FIG. 21 is a diagram illustrating an example of a screen according to an eleventh embodiment.

In an eleventh embodiment, screen information indicating the manipulation information is displayed by using a three-dimensional image. FIG. 21 is a diagram illustrating an example of a screen according to the eleventh embodiment.

As illustrated in FIG. 21, the screen displayed on the display device 3 based on the image information includes an endoscopic image and a navigation image showing the manipulation information of the next stage by using the three-dimensional image. For example, the navigation image is an image in which an object indicating an operation direction (manipulation information of the next stage) of the endoscope 1 is superimposed and displayed on a three-dimensional image virtually showing a hollow organ such as bronchi of the subject. The three-dimensional image may include an entire image showing the entire hollow organ and a lumen image showing a lumen (observation site) of the hollow organ according to a position and viewpoint direction of the endoscope 1. The lumen image corresponds to a virtual 3D endoscopic image.

The control unit 21 acquires the three-dimensional image of the hollow organ of the subject, which is generated in advance based on tomographic image data obtained by an ultrasonic diagnostic apparatus, an X-ray CT apparatus, or the like, and stores the three-dimensional image in the storage unit 22. The control unit 21 estimates the position and the viewpoint direction of the distal end of the endoscope 1 at the time when the endoscopic image is captured based on the detection value of the physical detection quantity device provided in the insertion tube 11. The control unit 21 specifies the three-dimensional image according to the estimated position and viewpoint direction. The control unit 21 generates the navigation image, in which an object indicating the manipulation information of the next stage is superimposed and displayed on the specified three-dimensional image. For example, a part of the manipulation information such as information regarding the treatment tool may be displayed at a position away from the three-dimensional image with text data or the like. The control unit 21 generates the screen information in which the endoscopic image is associated with the navigation image including the manipulation information of the next stage, and outputs the generated screen information to the display device 3.

In the above description, the processor 2 for an endoscope may change the screen information according to the manipulation level of the endoscope operator. For example, in a case where the manipulation level of the endoscope operator is specified as a beginner, the control unit 21 generates the screen information including the above-described navigation image. In a case where the manipulation level is specified as an expert, the control unit 21 may generate the screen information not including the navigation image. In a case where the manipulation level is specified as an expert, the control unit 21 may display the screen information including the navigation image when predetermined conditions are not satisfied. The fact that the predetermined conditions are not satisfied may include, for example, a fact that the operation direction (insertion direction) at a branch point is incorrect, a fact that the manipulation information of the next stage which is output from the learning model 522 is not matched with the actual operation data of the endoscope 1 in the next stage, and the like.

Figure 22:
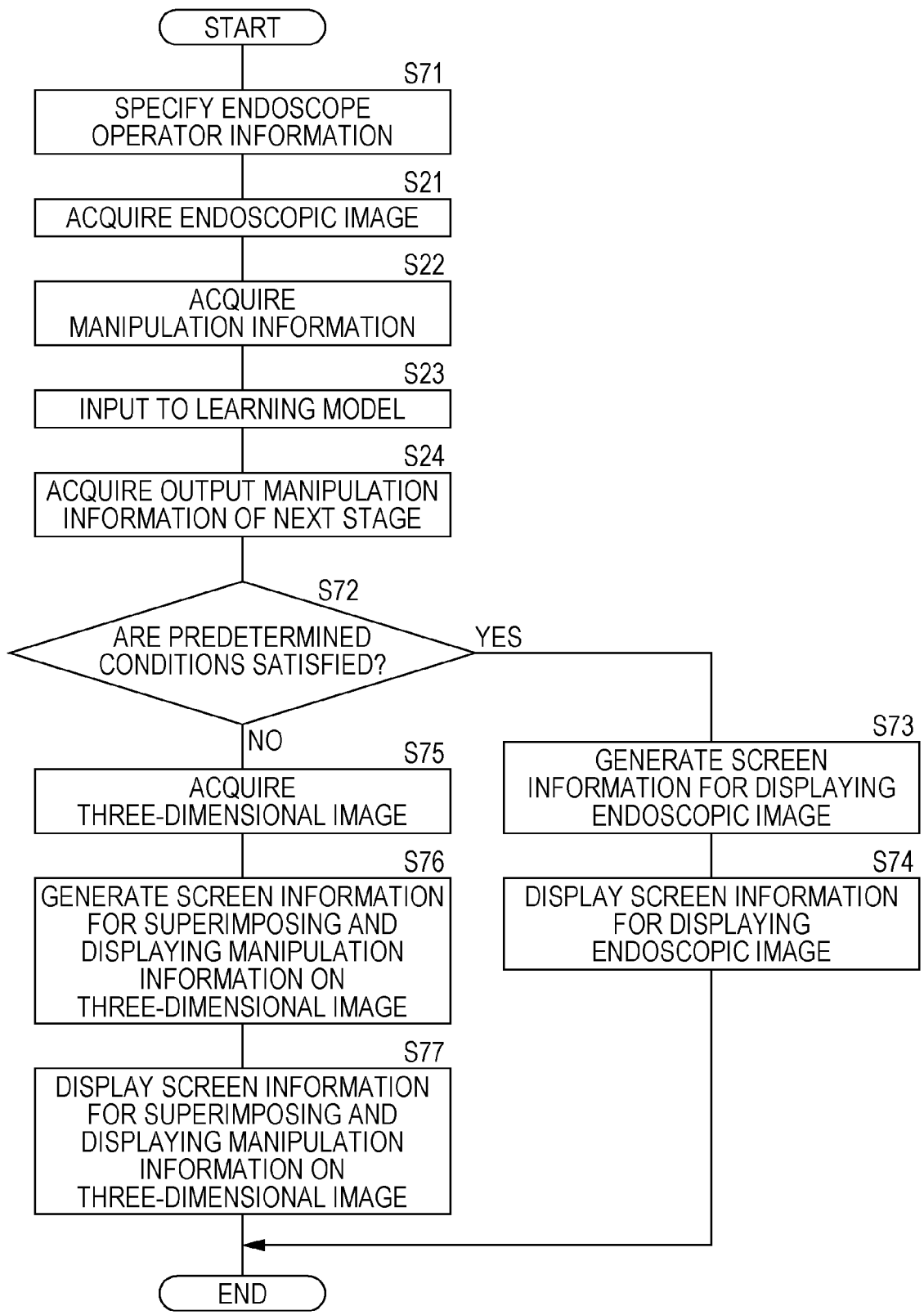
FIG. 22 is a flowchart illustrating an example of a processing procedure performed by a processor for an endoscope according to an eleventh embodiment.

FIG. 22 is a flowchart illustrating an example of a processing procedure performed by the processor 2 for an endoscope according to the eleventh embodiment. Processing common to those in FIG. 13 of the fifth embodiment are denoted by the same step numbers, and detailed descriptions thereof will be omitted.

For example, the control unit 21 of the processor 2 for an endoscope acquires the manipulation level of the endoscope operator by referring to the database (not illustrated) or the like that stores the endoscope operator information, and then specifies the manipulation level (endoscope operator information) (step S71).

The control unit 21 executes the processing from step S21 to step S24 illustrated in FIG. 13 and acquires the manipulation information of the next stage by using the learning model 522. The control unit 21 determines whether or not predetermined conditions are satisfied (step S72). For example, the control unit 21 determines whether or not the operation of the endoscope 1 is incorrect. In a case where it is determined that the operation is not incorrect, that is, the conditions are satisfied (step S72: NO), the control unit 21 generates the screen information for displaying the endoscopic image (step S73). The control unit 21 displays the screen information for displaying the generated endoscopic image by using the display device 3 (step S74), and ends the processing.

When it is determined that the operation is incorrect, that is, the conditions are not satisfied (step S72: YES), the control unit 21 estimates the position and viewpoint direction of the distal end of the endoscope 1 at the time of capturing the endoscopic image, and acquires the three-dimensional image corresponding to the estimated position and viewpoint direction (step S75). The control unit 21 generates the screen information for displaying the navigation image and the endoscopic image in association with each other, the navigation image being displayed by superimposing the manipulation information of the next stage on the acquired three-dimensional image (step S76). The control unit 21 displays the generated screen information by using the display device 3 (step S77), and ends a series of processing.

According to the present embodiment, since the manipulation information is displayed on the three-dimensional image, the manipulation information can be easily recognized. Furthermore, since the manipulation information corresponding to the manipulation level or the actual manipulation state of the endoscope operator is displayed, it is possible to more suitably support the manipulation of the endoscope operator.

Twelfth Embodiment

In a twelfth Embodiment, the processor 2 for an endoscope estimates the manipulation information of the next stage according to the type of the processor 2 for an endoscope by using the learning model 522.

The information processing device 5 generates a plurality of types of the learning models 522 corresponding to the type of the processor 2 for an endoscope. The processor 2 for an endoscope acquires the learning model 522 corresponding to the type of the processor 2 for an endoscope which corresponds to the apparatus itself and stores the learning model 522 in the storage unit 52. For example, in a case where the endoscopic image and the manipulation information including the light amount (light amount ratio) in the processor 2 for an endoscope and parameters related to the image processing are input, the learning model 522 outputs the manipulation information including the light amount (light amount ratio) in the next stage and the parameters related to the image processing.

For example, the processor 2 for an endoscope generates a white light image by white light for normal light observation by combining a semiconductor light source that emits blue light included in the light source 24 and a phosphor that emits yellow fluorescence. The processor 2 for an endoscope also generates a special light image by illumination light for special light observation by combining a semiconductor light source that emits blue light and a semiconductor light source that emits purple light. The special light observation is a technique of emphasizing and displaying a blood vessel or the like traveling in a deep portion of a mucous membrane, for example, by using illumination light with a narrow band.

The control unit 21 of the processor 2 for an endoscope generates an image that can be easily observed by the endoscope operator by controlling the light amount or the light amount ratio of light from the semiconductor light source or the phosphor, and the parameters related to the image processing. Even in a case where the same endoscope 1 is used, a spectrum distribution of the light emitted by the light source 24 varies depending on the type of the processor 2 for an endoscope to be used, and thus a color tone of the endoscopic image displayed on the display device 3 varies. Therefore, by changing the light amount (light amount ratio) and the parameters related to the image processing according to the type of the processor 2 for an endoscope, it is possible to improve visibility of the endoscope operator with respect to the generated endoscopic image and to support the improvement of accuracy of the manipulation. Note that the light amount to be output from the learning model 522 may be, for example, a light amount related to white light for normal light observation when being inserted to a predetermined site such as a cecum from the start of the examination, and a light amount related to illumination light for special light observation when being removed from the predetermined site.

The learning model 522 may include information regarding the type of the processor 2 for an endoscope as an input element and may output the output data corresponding to the type of the processor 2 for an endoscope. That is, in a case where the manipulation information including the light amount and the parameters related to the image processing, the endoscopic image, and the type of the processor 2 for an endoscope are input, the learning model 522 may output the manipulation information including the light amount and the parameters related to the image processing in the next stage.

The learning model 522 may also output the manipulation information including different light amount and different image processing parameters according to the manipulation level. For example, when the manipulation level of the endoscope operator is an expert, the learning model 522 outputs the manipulation information including the light amount and the image processing parameters which are suitable for generating a white light image in accordance with the white light for normal light observation. When the manipulation level is a beginner, the learning model 522 outputs the manipulation information including the light amount and the image processing parameters which are suitable for generating a special light image for highlighting a blood vessel or the like with the illumination light for special light observation. In a case where the manipulation level is a beginner, it is preferable that the control unit 21 automatically executes control of the light source 24 and image processing based on the output light amount and the output image processing parameters. The learning model 522 can output the manipulation information suitable for each manipulation level by performing the learning using the manipulation information corresponding to the manipulation level as the training data.

In the case of using the processor 2 for an endoscope including the light source 24 with the semiconductor light source, when the endoscope operator is an expert having long experience, the endoscopic image obtained by using a xenon lamp of the related art may be easier to observe. The learning model 522 may output the manipulation information including the light amount and the image processing parameters, which are suitable for generating an image similar to the endoscopic image obtained by using the xenon lamp, according to the manipulation level. Note that the control unit 21 may store, in the storage unit 22, the database (not illustrated) that stores correspondence information between the output data of the learning model 522 and the light amount and image processing parameters. The control unit 21 may generate an image suitable for the endoscope operator by executing conversion processing based on the light amount and the image processing parameters which are read from the database.

In the above-described processing, the endoscopic image input to the learning model 522 may be different from the endoscopic image displayed on the display device 3. For example, the control unit 21 executes processing based on the light amount and the image processing parameters of the next stage which are output from the learning model 522, and generates an endoscopic image for display in a state in which the endoscopic image is easily viewed by the endoscope operator. Furthermore, the control unit 21 executes processing based on image processing parameters different from the light amount and the image processing parameters of the next stage which are output from the learning model 522, and generates an input endoscopic image suitable for feature amount extraction by the learning model 522. The control unit 21 displays the generated endoscopic image for display on the display device 3, inputs the input endoscopic image to the learning model 522, and outputs the manipulation information of the next stage. Note that the input endoscopic image is only required to be an image on which processing based on the light amount and the image processing parameters of the next stage is not executed. That is, the input endoscopic image is not limited to an image on which new image processing is executed, and may be image data itself acquired from the image sensor of the endoscope 1.

According to the present embodiment, since the manipulation information corresponding to the processor 2 for an endoscope is output, convenience of the endoscope operator can be improved and the manipulation can be suitably supported.

Thirteenth Embodiment

Figure 23:
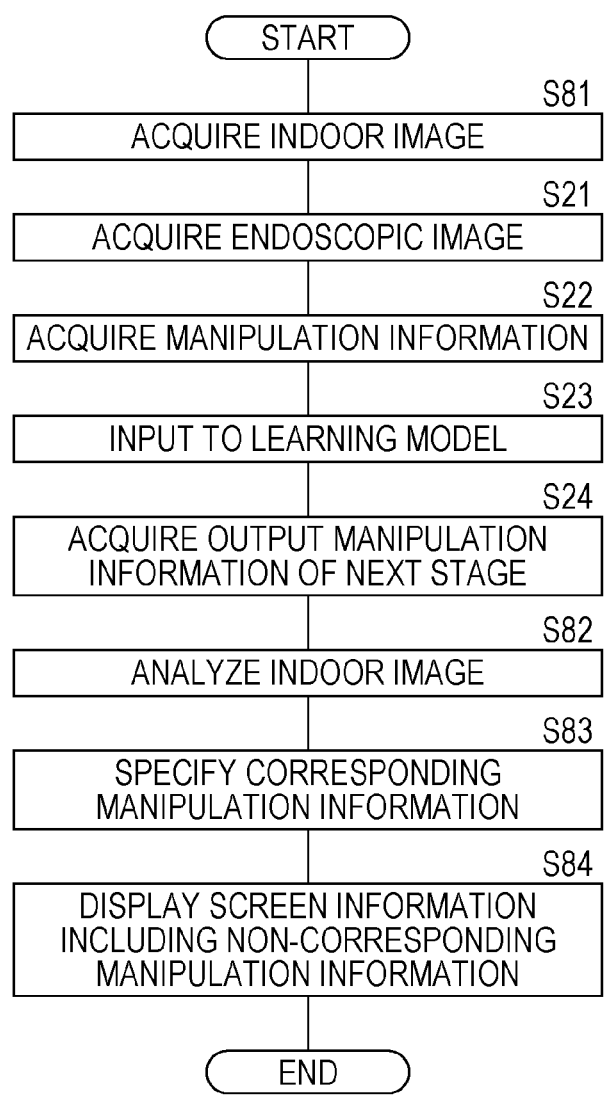
FIG. 23 is a flowchart illustrating an example of a processing procedure performed by a processor for an endoscope according to a thirteenth embodiment.

In a thirteenth embodiment, the output contents of the manipulation information are changed according to the manipulation state. FIG. 23 is a flowchart illustrating an example of a processing procedure executed by the processor 2 for an endoscope according to the thirteenth embodiment. Processing common to those in FIG. 13 of the fifth embodiment are denoted by the same step numbers, and detailed descriptions thereof will be omitted.

The control unit 21 of the processor 2 for an endoscope acquires the indoor image from the imaging device 6 (step S81). The imaging device 6 may include a voice input device such as a microphone and generate a moving image (indoor image) with voice with which time axes of the image data and the voice data are matched. The control unit 21 executes the processing from step S21 to step S24 illustrated in FIG. 13 and acquires the manipulation information of the next stage by using the learning model 522.

The control unit 21 analyzes the voice data of the indoor image (step S82). The control unit 21 specifies the corresponding manipulation information based on the analysis result (step S83). Specifically, the control unit 21 compares the analysis result of the voice data with the output data (manipulation information) of the learning model 522 to specify the output data matching with the analysis result. For example, in a case where the contents for instructing preparation of a predetermined treatment tool are included in the voice data, when the same treatment tool is included in the output data of the learning model 522, the treatment tool of the next stage is already prepared, and thus it is not necessary to display the manipulation information regarding the treatment tool. Note that the control unit 21 is not limited to the one that acquires the analysis result obtained by analysis processing of the voice data, and may acquire the analysis result obtained by an image analysis of the indoor image.

The control unit 21 generates the screen information that displays output data other than the output data that matches with the specified analysis result, that is, the manipulation information not corresponding and the endoscopic image in association with each other. The control unit 21 displays the generated screen information by using the display device 3 (step S84), and ends a series of processing.

In a case where the analysis result and the output data do not match with each other, when it is estimated that the voice data of the analysis result is incorrect, the control unit 21 may output screen information or a synthesized voice, which prompts a change of the treatment tool, such as "XX is better". In a case where the name of the treatment tool is included in the voice data, when the treatment tool of the voice data is different from the treatment tool output from the learning model 522, it is estimated that the instruction is incorrect. In this case, it is preferable to prevent omission of confirmation of the endoscope operator or the assistant by emphasizing and presenting a new treatment tool.

According to the present embodiment, by outputting information according to the state of the endoscope room by using the learning model 522, it is possible to more suitably support the manipulation.

Fourteenth Embodiment

In a fourteenth Embodiment, the endoscope 1 includes a time-of-flight (TOF) sensor, and a detection value obtained by the TOF sensor is included in the manipulation information. In the fourteenth Embodiment, the insertion tube 11 of the endoscope 1 includes the TOF sensor capable of detecting a distance to the object at the distal end thereof. The light source 24 of the processor 2 for an endoscope includes a light source that emits infrared light to be detected by the TOF sensor. The TOF sensor detects time until the infrared light emitted from light source 24 is reflected by the object and received. By using the TOF sensor, it is possible to acquire data regarding a distance from the distal end of the insertion tube 11 to the object (internal body site) and a shape of the object. The TOF sensor outputs the detection result to the processor 2 for an endoscope.

The learning model 522 of the fourteenth embodiment outputs the manipulation information of the next stage in a case where the manipulation information including the detection value obtained by the TOF sensor and the endoscopic image are input. The input detection value may be the detection value itself obtained by the TOF sensor, or may be data indicating a distance to or a shape of the object (lesion site as an observation site) obtained based on the detection value. According to the present embodiment, the learning model 522 can output the operation data of the distal end of the endoscope 1 with higher accuracy based on the manipulation information including the detection value obtained by the TOF sensor.

The embodiments disclosed herein are exemplary in all respects, and it should be considered that the embodiments are not restrictive. The technical features described in the embodiments can be combined with each other, and the scope of the present invention is intended to include all modifications within the scope of the claims and the scope equivalent to the claims.

REFERENCE SIGNS LIST

210 Manipulation support system
1 Endoscope
2 Processor for endoscope
21 Control unit
22 Storage unit
2P Program
3 Display device
4 Detection device
5 Information processing device
51 Control unit
52 Storage unit
5P Program
522 Learning model
523 Evaluation model 6 Imaging device
7 Visual line detection device

The invention claimed is:

1. A method for generating a learning model, the method comprising:
acquiring an endoscopic image captured by an endoscope and manipulation information regarding a manipulation of an endoscope operator in each stage of operation of the endoscope by the endoscope operator operating the endoscope;
generating a learning model learned so as to output the manipulation information of a next stage in a case where the endoscopic image and the manipulation information are input, based on training data including the acquired endoscopic image and manipulation information, and the manipulation information of the next stage;
specifying the manipulation level of the endoscope operator with respect to the manipulation of the endoscope;
displaying the manipulation information of the next stage, which is output from the learning model, in a case of a first manipulation level according to the specified manipulation level; and
in a case of a second manipulation level higher than the first manipulation level, not displaying the manipulation information of the next stage, which is output from the learning model, when predetermined conditions are satisfied, and displaying the manipulation information of the next stage, which is output from the learning model, when the predetermined conditions are not satisfied.

2. The method for generating a learning model according to claim 1, further comprising:
acquiring the manipulation information indicating state data of both arms and both hands of the endoscope operator by using a 3D laser sensor; and
generating the learning model learned so as to output the manipulation information indicating the state data of both arms and both hands of the next stage in a case where the endoscopic image and the manipulation information indicating the state data of both arms and both hands are input to the learning model.

3. The method for generating a learning model according to claim 1, further comprising:
acquiring the manipulation information indicating operation data of a distal end of the endoscope; and
generating the learning model learned so as to output the manipulation information indicating the operation data of the distal end of the endoscope of the next stage in a case where the endoscopic image and the manipulation information indicating the operation data of the distal end of the endoscope are input to the learning model.

4. The method for generating a learning model according to claim 1, further comprising:
generating the learning model learned so as to output an image based on the manipulation information indicating the state data of both arms and both hands of the next stage in a case where the endoscopic image and the manipulation information indicating the state data of both arms and both hands are input to the learning model.

5. The method for generating a learning model according to claim 1, further comprising:
acquiring an indoor image from an imaging device that captures the indoor image including the endoscope operator; and
generating the learning model learned so as to output the manipulation information of the next stage in a case where the endoscopic image, the manipulation information, and the indoor image are input to the learning model, based on the training data including the acquired endoscopic image, manipulation information, and indoor image, and the manipulation information of the next stage.

6. The method for generating a learning model according to claim 1, further comprising:
acquiring visual line data of the endoscope operator; and
generating the learning model learned so as to output the manipulation information and visual line data of the next stage in a case where the endoscopic image, the manipulation information, and the visual line data are input to the learning model, based on the training data including the acquired endoscopic image, manipulation information, and visual line data, and the manipulation information and visual line data of the next stage.

7. The method for generating a learning model according to claim 1, further comprising
generating a plurality of types of the learning models according to a manipulation level of the endoscope operator with respect to the manipulation of the endoscope.

8. The method for generating a learning model according to claim 1, further comprising
generating a plurality of types of the learning models according to a body type of the endoscope operator.

9. The method for generating a learning model according to claim 1, further comprising:
acquiring the manipulation information including a light amount and parameters related to image processing in a processor for an endoscope, the processor acquiring the endoscopic image captured by the endoscope; and
generating the learning model learned so as to output the manipulation information including the light amount and the parameters related to the image processing in the next stage, in a case where the endoscopic image and the manipulation information including the light amount and the parameters related to the image processing are input to the learning model.

10. A non-transitory computer-readable medium containing a program causing a computer to execute processing comprising:
acquiring an endoscopic image captured by an endoscope and manipulation information regarding a manipulation of an endoscope operator in each stage of operation of the endoscope by the endoscope operator operating the endoscope; and
inputting the acquired endoscopic image and manipulation information to a learning model learned so as to output the manipulation information of a next stage and outputting the manipulation information of the next stage in a case where the endoscopic image and the manipulation information are input, based on training data including the endoscopic image and manipulation information, and the manipulation information of the next stage;
specifying the manipulation level of the endoscope operator with respect to the manipulation of the endoscope;
displaying the manipulation information of the next stage, which is output from the learning model, in a case of a first manipulation level according to the specified manipulation level; and
in a case of a second manipulation level higher than the first manipulation level, not displaying the manipulation information of the next stage, which is output from the learning model, when predetermined conditions are satisfied, and displaying the manipulation information of the next stage, which is output from the learning model, when the predetermined conditions are not satisfied.

11. The non-transitory computer-readable medium containing a program according to claim 10, causing a computer to execute the processing further comprising:
acquiring the manipulation information indicating state data of both arms and both hands of the endoscope operator by using a 3D laser sensor; and
inputting, to the learning model, the acquired endoscopic image and the acquired manipulation information indicating the state data of both arms and both hands, and outputting the manipulation information indicating the state data of both arms and both hands of the next stage.

12. The non-transitory computer-readable medium containing a program according to claim 10, causing a computer to execute the processing further comprising:
acquiring the manipulation information indicating operation data of a distal end of the endoscope; and
inputting, to the learning model, the acquired endoscopic image and the acquired manipulation information indicating the operation data of the distal end of the endoscope, and outputting the manipulation information indicating the operation data of the distal end of the endoscope of the next stage.

13. The non-transitory computer-readable medium containing a program according to claim 10, causing a computer to execute the processing further comprising:
causing the learning model to be learned so as to output an image based on the manipulation information indicating the state data of both arms and both hands of the next stage in a case where the endoscopic image and the manipulation information indicating the state data of both arms and both hands are input;
acquiring the manipulation information indicating the state data of both arms and both hands of the endoscope operator; and
inputting, to the learning model, the acquired endoscopic image and the acquired manipulation information indicating the state data of both arms and both hands, and outputting the image based on the manipulation information indicating the state data of both arms and both hands of the next stage.

14. The non-transitory computer-readable medium containing a program according to claim 10, causing a computer to execute the processing further comprising:
acquiring an indoor image from an imaging device capturing the indoor image including the endoscope operator; and
inputting the acquired endoscopic image, the acquired manipulation information, and the acquired indoor image to the learning model learned so as to output the manipulation information of the next stage, and outputting the manipulation information of the next stage in a case where the endoscopic image, the manipulation information, and the indoor image are input, based on the training data including the endoscopic image, manipulation information and indoor image, and the manipulation information of the next stage.

15. The non-transitory computer-readable medium containing a program according to claim 10, causing a computer to execute the processing further comprising:
acquiring visual line data of the endoscope operator; and
inputting the acquired endoscopic image, the acquired manipulation information, and the acquired visual line data to the learning model learned so as to output the manipulation information and visual line data of the next stage, and outputting the manipulation information and visual line data of the next stage in a case where the endoscopic image, the manipulation information, and the visual line data are input, based on the training data including the endoscopic image, manipulation information, and visual line data, and the manipulation information and visual line data of the next stage.

16. The non-transitory computer-readable medium containing a program according to claim 10, causing a computer to execute the processing further comprising:
specifying a manipulation level of the endoscope operator with respect to the manipulation of the endoscope; and
selecting, from a plurality of types of the learning models prepared according to the manipulation level, the learning model corresponding to the specified manipulation level of the endoscope operator with respect to the manipulation of the endoscope.

17. The non-transitory computer-readable medium containing a program according to claim 10, causing a computer to execute the processing further comprising
specifying the manipulation level of the endoscope operator with respect to the manipulation of the endoscope in parallel with output of the manipulation information.

18. The non-transitory computer-readable medium containing a program according to claim 10, causing a computer to execute the processing further comprising:
acquiring the indoor image from the imaging device capturing the indoor image including the endoscope operator;
specifying, based on the acquired indoor image, the corresponding manipulation information among the manipulation information of the next stage, which is output from the learning model; and
displaying the manipulation information of the next stage, which is output from the learning model excluding the specified corresponding manipulation information.

19. The non-transitory computer-readable medium containing a program according to claim 10, causing a computer to execute the processing further comprising
outputting screen information for superimposing and displaying the manipulation information of the next stage on a three-dimensional image showing a hollow organ of a subject.

* * * * *